US012788234B2

(12) United States Patent
Westwick et al.

(10) Patent No.: US 12,788,234 B2
(45) Date of Patent: Nov. 10, 2026

(54) CONTRAST ENHANCEMENT FOR MEDICAL IMAGING

(71) Applicant: Stryker Corporation, Portage, MI (US)

(72) Inventors: Paul Roald Westwick, Vancouver (CA); Xudong Lu, West Vancouver (CA); Arthur E. Bailey, North Vancouver (CA); John J.P. Fengler, North Vancouver (CA)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 19/322,632

(22) Filed: Sep. 8, 2025

(65) Prior Publication Data

US 2026/0000283 A1 Jan. 1, 2026

Related U.S. Application Data

(63) Continuation of application No. 17/561,658, filed on Dec. 23, 2021, now Pat. No. 12,433,477.

(60) Provisional application No. 63/132,440, filed on Dec. 30, 2020.

(51) Int. Cl.

| | |
|---|---|
| ***A61B 1/00*** | (2006.01) |
| ***A61B 1/04*** | (2006.01) |
| ***A61B 1/06*** | (2006.01) |
| ***A61B 5/00*** | (2006.01) |
| ***A61K 49/00*** | (2006.01) |

(52) U.S. Cl.

CPC ............ *A61B 1/043* (2013.01); *A61B 1/0005* (2013.01); *A61B 1/0638* (2013.01); *A61B 5/0071* (2013.01); *A61K 49/0034* (2013.01)

(58) Field of Classification Search

None

See application file for complete search history.

(56) References Cited

U.S. PATENT DOCUMENTS

| | | | |
|---|---|---|---|
| 7,722,534 | B2 | 5/2010 | Cline |
| 9,173,554 | B2 | 11/2015 | Fengler |
| 2002/0093563 | A1 | 7/2002 | Cline et al. |

(Continued)

OTHER PUBLICATIONS

International Preliminary Report on Patentability dated Jul. 4, 2023, directed to International Application No. PCT/US2021/073102; 13 pages.

(Continued)

*Primary Examiner* — Amal Aly Farag

(74) *Attorney, Agent, or Firm* — Morrison & Foerster LLP

(57) ABSTRACT

A method of visualizing tissue of a subject includes receiving a fluorescence image of the tissue including a plurality of intensity values. A first portion of the intensity values is associated with a first fluorescence emission that is from fluorescence agent that is preferentially accumulated or activated in a target region in the tissue, and a second portion of the intensity values is associated with a second fluorescence emission that is from fluorescence agent that is not located within the target region. The intensity values are analyzed to determine a set of local maximum intensity values. An enhanced fluorescence image is generated by applying a nonlinear contrast mapping based on the set of local maximum intensity values to the plurality of intensity values. The enhanced fluorescence image is displayed, and at least a portion of the target region is diagnosed or treated based on the displayed enhanced fluorescence image.

20 Claims, 11 Drawing Sheets
(2 of 11 Drawing Sheet(s) Filed in Color)

(56) References Cited

U.S. PATENT DOCUMENTS

| | | | |
|---|---|---|---|
| 2004/0116808 | A1 | 6/2004 | Fritz |
| 2010/0106026 | A1 | 4/2010 | Benaron |
| 2011/0164127 | A1 | 7/2011 | Stehle et al. |
| 2011/0237895 | A1 | 9/2011 | Yoshida |
| 2014/0276103 | A1 | 9/2014 | Lee |
| 2015/0182118 | A1 | 7/2015 | Bradbury |

OTHER PUBLICATIONS

International Search Report and Written Opinion mailed Apr. 25, 2022, directed to International Application No. PCT/US2021/073102; 18 pages.
Office Action dated Jun. 30, 2025, directed to EP Application No. 21848508.4; 6 pages.
Westwick et al., U.S. Notice of Allowance and Fee(s) Due mailed Jun. 6, 2025, directed to U.S. Appl. No. 17/561,568; 13 pages.
Westwick et al., U.S. Office Action dated Aug. 26, 2024, directed to U.S. Appl. No. 17/561,658; 22 pages.
Westwick et al., U.S. Restriction/Election of Species Requirement dated Feb. 1, 2024, directed to U.S. Appl. No. 17/561,658; 9 pages.

CONTRAST ENHANCEMENT FOR MEDICAL IMAGING

CROSS-REFERENCE TO RELATED APPLICATIONS

This application is a continuation of U.S. patent application Ser. No. 17/561,658, filed Dec. 23, 2021, which claims the benefit of U.S. Provisional Application No. 63/132,440, filed Dec. 30, 2020, the entire contents of each of which are hereby incorporated by reference herein.

FIELD

The present disclosure relates generally to medical imaging, and more particularly to acquiring and processing medical images for visualizing tissue of a subject.

BACKGROUND

Medical imaging systems (e.g., endoscopic imaging systems for minimally-invasive surgery or open field medical imaging systems) can help provide clinical information for medical practitioners who need to make decisions (e.g. intraoperative or treatment decisions) based on visualization of tissue. In many applications, it is useful for medical imaging systems to provide fluorescence imaging for visualization of tissue that cannot be visualized or is poorly visualized with white light imaging. Fluorescence imaging generally involves the administration of a bolus of an imaging agent that circulates throughout the subject's tissue or local administration of an imaging agent in a region of the subject's tissue, and the imaging agent emitting a fluorescence signal when illuminated with the appropriate excitation light. Fluorescence imaging systems acquire images of the emitted imaging agent fluorescence as the imaging agent bolus traverses the subject's tissue in the imaging field of view. When the images are displayed on a display, clinicians may observe the imaging agent as well as differences in fluorescence intensity associated with the imaging agent in the imaging field of view. Based on their visual perception of the fluorescence intensity, clinicians may make qualitative determinations regarding the tissue in the imaging field of view.

Targeted fluorescence imaging agents have been developed to localize in specific tissue structures, such as tumors, to aid in the identification of those structures using fluorescence imaging. Localized areas of high intensity in fluorescence images of targeted fluorescence imaging agents may indicate the presence of targeted tissue structures in the imaging field of view. However, targeted imaging agents may sometimes remain in significant concentrations in non-targeted areas of tissue. Therefore, although the most intensely fluorescent area of an image may be associated with targeted tissue structures, there may also be substantial fluorescence signal from imaging agent that remains circulating in surrounding tissue. As a result, the contrast between the targeted tissue and non-targeted tissue may be reduced, limiting a surgeon's ability to identify and localize the targeted tissue.

SUMMARY

According to an aspect, systems and methods enhance the contrast in a fluorescence image between targeted and non-targeted regions of the tissue, which can help a clinician better identify and localize the targeted tissue. Optionally, a fluorescence image of the tissue of a subject generated from the fluorescence emission of a targeted fluorescence agent is enhanced by applying a contrast enhancing transform to at least some of the intensity values in the image. Optionally, a threshold intensity value is determined based on the un-enhanced fluorescence image and values below the threshold intensity are reduced according to the transform algorithm. The enhanced fluorescence image can be displayed to a clinician for visualizing the targeted region of tissue.

According to an aspect, a method of visualizing tissue of a subject includes receiving a fluorescence image of the tissue of the subject, wherein the fluorescence image comprises a plurality of intensity values, a first portion of the intensity values are associated with a first fluorescence emission that is from fluorescence agent that is preferentially accumulated or activated in a target region in the tissue and a second portion of the intensity values are associated with a second fluorescence emission that is from fluorescence agent that is not located within the target region in the tissue; generating an enhanced fluorescence image by reducing one or more of the intensity values that are below a threshold intensity value to increase contrast between the target region in the tissue and areas that are associated with the fluorescence agent that is not located within the target region in the tissue; and displaying the enhanced fluorescence image.

Optionally, the method can include prior to generating the enhanced fluorescence image, determining the threshold intensity value based on the fluorescence image.

Optionally, the method can include, prior to generating the enhanced fluorescence image, determining the threshold intensity value based on one or more fluorescence images generated prior to the received fluorescence image.

Optionally, an amount of reduction of at least one intensity value is based on a magnitude of the at least one intensity value.

Optionally, one or more of the intensity values that are reduced includes intensity values in the second portion of the intensity values. One or more of the intensity values that are reduced may include intensity values in the first portion of the intensity values.

Optionally, the threshold intensity value is based on a percentage of intensity values in the fluorescence image that are equal to or below a predefined percentile. The percentage may be at least 75% and the corresponding predefined percentile may be at least the 75th.

Optionally, the threshold intensity value is based on a maximum intensity value in the fluorescence image. The threshold intensity value may be a predefined percentage of the maximum intensity value. The predefined percentage may be at least 75%.

Optionally, at least some of the intensity values are unchanged in the enhanced fluorescence image.

Optionally, generating the enhanced fluorescence image comprises increasing one or more intensity values that are above the threshold intensity value.

Optionally, the one or more of the intensity values are reduced using a power function. The power function may be based on a power of at least 2.

Optionally, the method includes illuminating the tissue with fluorescence excitation light.

Optionally, the method includes receiving fluorescence emission from the fluorescence agent that is preferentially accumulated or activated in the target region in the tissue and from fluorescence agent that is not located within the target region in the tissue. The method may include receiving the fluorescence emission using an endoscope. The endoscope may be pre-inserted into the body of a patient prior to receiving the fluorescence emission. The method may include receiving the fluorescence emission using an open field imager.

Optionally, the method includes locating an area of the tissue having the target cells based on the displayed enhanced fluorescence image.

Optionally, the enhanced fluorescence image is displayed in combination with a visible light image. The visible light image may be a white light image. Displaying the enhanced fluorescence image may include at least one of overlaying the enhanced fluorescence image on the visible light image, displaying the enhanced fluorescence image picture in picture, and displaying the enhanced fluorescence image side by side with the visible light image.

Optionally, the fluorescence image was generated by an imager and the fluorescence image comprises imager pixel intensity values.

Optionally, the fluorescence image is based on an image generated by a fluorescence imager.

Optionally, a number of intensity values in the fluorescence image is different than a number of pixels in the fluorescence imager.

Optionally, at least one of the fluorescence agent that is preferentially accumulated or activated in a target region in the tissue and the fluorescence agent that is not located within the target region in the tissue comprises at least one of Indocyanine green, Methylene Blue, proflavine, aminolevulinic acid or a derivative or product thereof, hexaminolevulinate, methyl aminolevulinate, a cathepsin activatable probe, a protease activatable probe, fluorescent lectin, an HSP90 inhibitor, a chlorotoxin, 7-aa peptide-IRDye800CW, a c-Met targeting peptide, a folate receptor targeter, a tumor-specific integrin receptor binder, an anti-EGFR binding peptide, an anti-EGFR affibody, a GRPR receptor binding peptide, a VEGF antibody, an EGFR antibody, and a carbonic anhydrase IX antibody.

Optionally, the fluorescence agent that is preferentially accumulated or activated in a target region in the tissue and the fluorescence agent that is not located within the target region in the tissue are the same type of fluorescence agent.

Optionally, the fluorescence image is received from an imager.

Optionally, the fluorescence image is received from a memory.

Optionally, the enhanced fluorescence image is displayed during a surgical procedure on the subject. The surgical procedure can be a prostate or a spinal surgery and the target region may include a nerve; the surgical procedure can be a lower pelvic surgery and the target region can include a ureter; the surgical procedure can be a hepatobiliary surgery and the target region can include a biliary duct; and the surgical procedure can include a tumor removal and the target region can include the tumor. It is noted that the method concerns the processing of fluorescence images. There is no functional link between the method and effects produced on the body. The method is not a method of treatment of the body.

Optionally, the fluorescence image is a video frame.

Optionally, the fluorescence agent that is preferentially accumulated or activated in a target region in the tissue is bound to cells targeted by the fluorescence agent and the fluorescence agent that is not located within the target region in the tissue is not bound to cells targeted by the fluorescence agent.

Optionally, the region targeted by the fluorescence agent comprises at least one of a tumor, a nerve, a ureter, and a biliary duct.

According to an aspect, a system for visualizing tissue of a subject includes a display; one or more processors; memory; and one or more programs, wherein the one or more programs are stored in the memory and configured to be executed by the one or more processors, the one or more programs including instructions for: receiving a fluorescence image of the tissue of the subject, wherein the fluorescence image comprises a plurality of intensity values, a first portion of the intensity values are associated with a first fluorescence emission that is from fluorescence agent that is preferentially accumulated or activated in a target region in the tissue and a second portion of the intensity values are associated with a second fluorescence emission that is from fluorescence agent that is not located within the target region in the tissue; generating an enhanced fluorescence image by reducing one or more of the intensity values that are below a threshold intensity value to increase contrast between the target region in the tissue and areas that are associated with the fluorescence agent that is not located within the target region in the tissue; and displaying the enhanced fluorescence image.

Optionally, the system includes a light source for providing fluorescence excitation light to the tissue of the subject.

Optionally, the system includes an imager for generating the fluorescence image. The imager may be an endoscopic imager or an open field imager.

Optionally, the one or more programs further include instructions for, prior to generating the enhanced fluorescence image, determining the threshold intensity value based on the fluorescence image.

Optionally, the one or more programs further include instructions for, prior to generating the enhanced fluorescence image, determining the threshold intensity value based on one or more fluorescence images generated prior to the received fluorescence image.

Optionally, an amount of reduction of at least one intensity value is based on a magnitude of the at least one intensity value.

Optionally, one or more of the intensity values that are reduced includes intensity values in the second portion of the intensity values. One or more of the intensity values that are reduced may include intensity values in the first portion of the intensity values.

Optionally, the threshold intensity value is based on a percentage of intensity values in the fluorescence image that are equal to or below a predefined percentage. The predefined percentage may be at least 75%.

Optionally, the threshold intensity value is based on a maximum intensity value in the fluorescence image. The threshold intensity value may be a predefined percentage of the maximum intensity value. The predefined percentage may be at least 75%.

Optionally, at least some of the intensity values are unchanged in the enhanced fluorescence image.

Optionally, one or more programs include instructions for generating the enhanced fluorescence image by increasing one or more intensity values that are above the threshold intensity value.

Optionally, one or more programs include instructions for reducing the one or more of the intensity values using a power function. The power function may be based on a power of at least 2.

Optionally, one or more programs include instructions for displaying the enhanced fluorescence image in combination with a visible light image. The visible light image may be a white light image. Displaying the enhanced fluorescence image may include at least one of overlaying the enhanced fluorescence image on the visible light image, displaying the enhanced fluorescence image picture in picture, and displaying the enhanced fluorescence image side by side with the visible light image.

According to an aspect, a non-transitory computer readable storage medium stores one or more programs for execution by one or more processors of a system for visualizing tissue of a subject, and the one or more programs include instructions for performing any of the methods above. According to an aspect, a computer program product is provided comprising instructions which, when executed by one or more processors of a system for visualizing tissue of a subject, cause the system to perform any of the methods above.

According to an aspect, a kit for imaging tissue includes a fluorescence imaging agent and any one of the systems above.

According to an aspect, a fluorescence imaging agent is used with any of the methods above for imaging tissue.

It will be appreciated that any of the variations, aspects, features and options described in view of the systems apply equally to the methods and vice versa. It will also be clear that any one or more of the above variations, aspects, features and options can be combined.

BRIEF DESCRIPTION OF THE FIGURES

The patent or application file contains at least one drawing executed in color. Copies of this patent or patent application publication with color drawing(s) will be provided by the Office upon request and payment of the necessary fee.

Features will become apparent to those of ordinary skill in the art by describing in detail exemplary examples with reference to the attached drawings in which.

DETAILED DESCRIPTION

Figure 1:
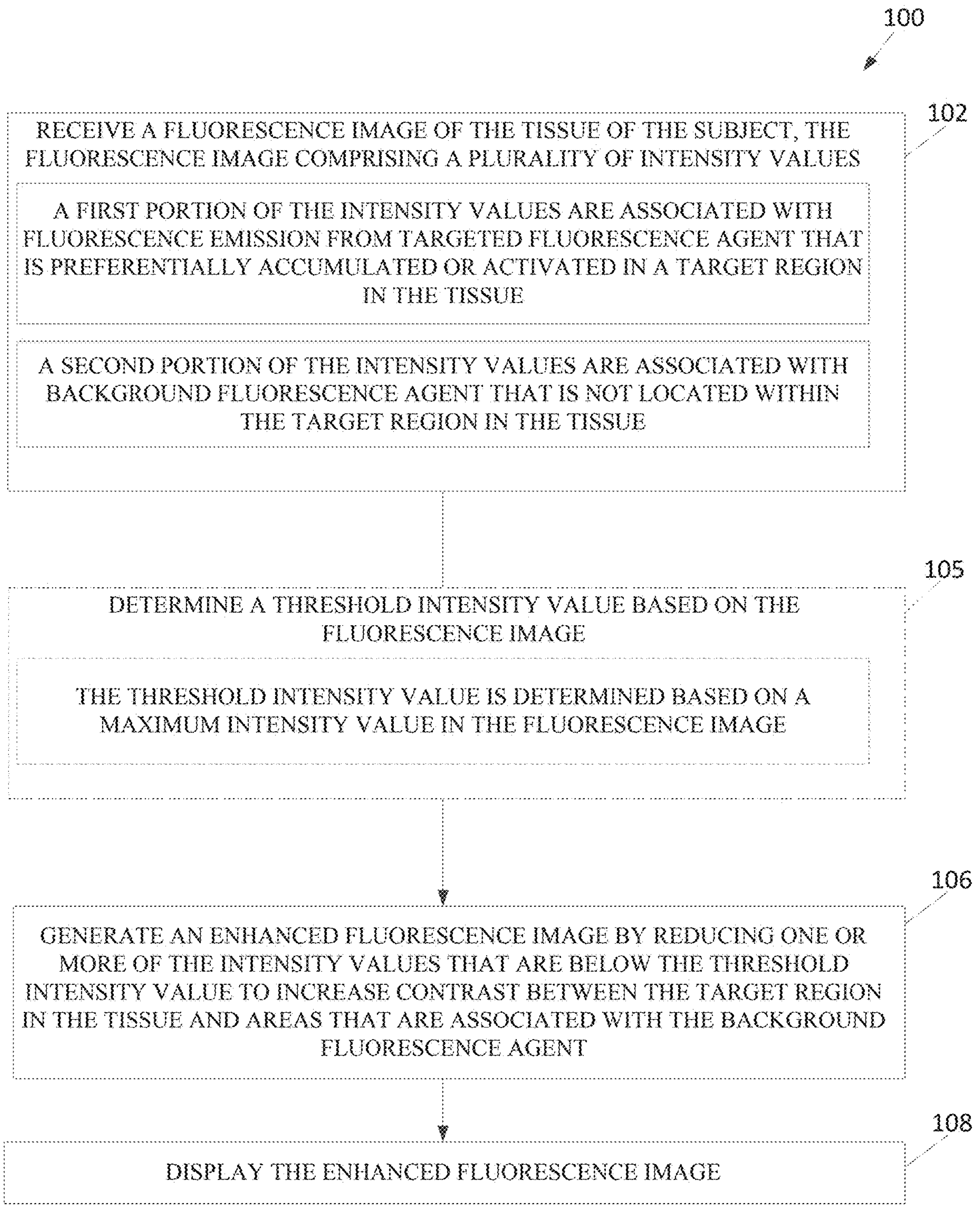
FIG. 1 shows an exemplary method for enhancing the contrast in a fluorescence image that captures a targeted fluorescence agent.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Described herein, according to various aspects, are systems and methods for enhancing visualization of targeted regions of tissue of a subject by increasing contrast in fluorescence images of tissue of a subject between areas associated with regions of tissue targeted by a fluorescent imaging agent and areas associated with regions of the tissue that are not targeted by the fluorescence imaging agent. Enhanced fluorescence images having higher contrast between targeted and non-targeted regions are generated by suppressing intensity values that are associated with non-targeted portions of the tissue such that the areas associated with targeted portions of the tissue become more prominent in the fluorescence image. Intensity values can be suppressed based on a peak or other threshold level of intensity in the image based on the notion that targeted regions of tissue captured in the image will be the brightest areas of the image. In some examples a nonlinear transform can be used to suppress intensity values that are below the threshold level of intensity such that intensity values that are nearer to the threshold intensity are suppressed to a greater degree, creating a significant increase in contrast between areas having intensities at or above the threshold intensity and areas having intensities below the threshold.

Many imaging agents that are configured for targeting certain regions of tissue should remain in circulation in the body long enough to sufficiently accumulate at the target. As a result of the requirement to remain in circulation, there may be some proportion of imaging agent that is present in an imaging field of view that is not at the target and provides what can be regarded as background noise in fluorescence images of the field of view. This background noise can obscure visualization of the target. Similarly, some imaging agents are configured to activate in the presence of the target, often in response to environmental conditions such as pH level or the presence of enzymes, and the environmental conditions may be present to some lesser degree in non-targeted regions, resulting in background fluorescence. The systems and methods described herein can be used to increase the contrast between the background fluorescence and the target fluorescence, helping a clinician to more easily visualize and localize the target.

In some examples, targeted imaging, according to the methods and systems described herein, can be performed in any surgical procedure involving: (a) sensitive, but difficult to see anatomy, including nerves or vessels such as ureters and biliary ducts as well as some blood and lymphatic vessels; and/or (b) difficult to visualize pathology that is to be treated or excised, including cancerous cells and other forms of diseased tissue. As such, targeted imaging according to examples described herein can be performed in any surgery in which there is a concern based on (a) or (b). A few examples of targeted tissue and the surgical procedures they may involve include nerves in prostate and spinal surgeries, ureters in lower pelvic surgeries such as colorectal and gynecological surgeries, biliary ducts in any hepatobiliary surgery, and cancers in any surgery for the removal of a cancerous tumor. Systems and methods described herein can be used to enhance visualization of any of these targets during the respective surgical procedures.

In the following description of the various examples, reference is made to the accompanying drawings, in which are shown, by way of illustration, specific examples that can be practiced. It is to be understood that other examples and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMS, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

Methods for Displaying Enhanced Florescence Images of a Target

FIG. 1 illustrates a method 100 for generating an enhanced fluorescence image for improving the visualization of target regions of tissue, according to some examples. Method 100 includes increasing the contrast in a fluorescence image between areas associated with the emission of fluorescence imaging agent in a targeted region of tissue and areas associated with the emission of fluorescence imaging agent that is not in the targeted region of tissue. Method 100 may be performed by an imaging system, such as an imaging system that includes an imager for generating fluorescence images and one or more processors for processing the images according to method 100. In some examples, method 100 is performed by an image processing system that receives one or more images from an imaging system and/or from a memory in which one or more images are stored.

At step 102, a fluorescence image of the tissue of a subject is received. The fluorescence image may be received from an imager or imaging system or may be received from a memory in which a previously generated image is stored. The fluorescence image can be a video frame or a single image. As used herein, the term fluorescence image covers both single images and video frames. The fluorescence image includes a plurality of intensity values that are proportional to fluorescence emission from one or more fluorescence agents present in the tissue of the subject at the time that the image was generated. A first portion of the intensity values are associated with fluorescence emission from fluorescence agent that is preferentially accumulated or activated in a target region in the tissue and a second portion of the intensity values are associated with fluorescence agent that is not located within the target region in the tissue.

The first portion of the intensity values are associated with the region of the imaged tissue that the fluorescence agent is configured to target. A fluorescence imaging agent can be configured to target a tissue in a number of ways. For example, a fluorescence agent can be configured to preferentially accumulate in a tissue, such as a tumor, by binding to cells of the tissue.

In some examples, the fluorescence agent targets a tissue by activating in the presence of the targeted tissue. So, while the fluorescence agent may be present in non-targeted tissue, the agent fluoresces (or fluoresces more) when in the presence of the targeted tissue and does not fluoresce (or fluoresces less) when in the non-targeted tissue.

The first portion of intensity values may be from a contiguous portion of the image or may be from multiple separate portions of the image. The first portion of intensity values will generally be the brightest intensity values in the image, representing regions of the tissue where the most imaging agent is present.

Some fluorescence agent may be present in other areas within the imaging field of view that are not the region targeted by the fluorescence agent. For example, the fluorescence agent that is preferentially accumulated or activated in a target region in the tissue can be an agent that binds to specific cells and some amount of the agent that is not bound to the cells may be located within the imaging field of view. The second portion of the intensity values are associated with these areas of the imaged tissue—areas that include fluorescence agent but do not include the targeted regions of tissue. Fluorescence in these non-targeted areas can be thought of as background fluorescence. Fluorescence emission from this background fluorescence will generally be lower in intensity than the fluorescence emission of the fluorescence agent in the targeted regions of tissue, but may be present in a sufficient amount to lead to poor contrast between the targeted regions and surrounding non-targeted regions in the fluorescence image.

At step 104, an enhanced fluorescence image is generated by reducing one or more of the intensity values that are below a threshold intensity value to increase contrast between areas of the image that are associated with the target region in the tissue and areas that are associated with non-targeted regions of the tissue. In some examples, the threshold intensity value is set so that when the targeted region of tissue is in the imaging field of view, at least some portion of the intensity values associated with the target region will be above the threshold intensity value and at least a majority of the intensity values associated with background fluorescence will be below the threshold intensity value.

By reducing one or more intensity values that are below the threshold intensity value, portions of the image that are associated with non-targeted regions of tissue become relatively dimmer in comparison to portions of the image that are associated with target regions of tissue. As such, at least some of the intensity values in the second portion of intensity values—those associated with the second fluorescence emission that is from fluorescence agent that is not located within the target region in the tissue—are reduced in generating the enhanced fluorescence image. In some examples, one or more intensity values in the first portion of the intensity values—those associated with the first fluorescence emission that is from fluorescence agent that is preferentially accumulated or activated in a target region in the tissue—may also be reduced. For example, a given area within the target region of tissue may not have as much accumulated fluorescence agent as another area within the target region and, as a result, may have intensity values that are below the threshold intensity, resulting in those intensity values being reduced in generating the enhanced image.

In some examples, the threshold intensity is a predetermined value. For example, the threshold intensity can be an intensity known to be associated with fluorescence emission of fluorescence agent present in a targeted region of tissue, such as determined through a clinical study. In some examples, the threshold intensity is based on a maximum possible intensity value for the imager or imaging system configuration.

In some examples, method 100 includes determining, at step 105, the threshold intensity based on one or more received fluorescence images. In some examples, the threshold intensity can be determined based on the fluorescence image for which the enhanced fluorescence image is generated in step 104. The threshold intensity may be determined based on the range of intensity values in the image. The threshold intensity value can be a predefined percentage of the maximum fluorescence intensity in the image. For example, the threshold intensity value may be 98% of the maximum fluorescence intensity in the image. In some examples, the threshold intensity value is associated with a percentile of intensity values in the image. For example, the threshold intensity value may be the intensity value that is greater than or equal to the intensity values of 98% of the pixels in the image. The predefined percentage can be at least 75%, at least 80%, at least 85%, at least 90%, at least 95%, at least 98%, or at least 99%. The predefined percentile value can be at least the $75^{th}$, at least the $80^{th}$, at least the $85^{th}$, at least the $90^{th}$, at least the $95^{th}$, at least the $98^{th}$, or at least the $99^{th}$.

In some examples, the threshold intensity is determined based on more than one fluorescence image, which may be particularly useful when enhancing video frames. The threshold intensity may be determined based on the currently received fluorescence image (the image for which the enhanced image is generated) and a predetermined number of previously generated fluorescence images. For example, the current fluorescence image in addition to the previous image (or any suitable number of previously generated images) may be used to determine the threshold intensity. In some examples, a threshold intensity determined for a set of fluorescence images can be the intensity that is greater than or equal to the predefined percentage of intensities in all of the fluorescence images in the set. In some examples, a threshold intensity can be an average of threshold intensities that are determined separately for each fluorescence image. For example, a percentile intensity (e.g., $95^{th}$ percentile or $98^{th}$ percentile) can be determined for a currently generated fluorescence image and this percentile intensity can be averaged with percentile intensities from a predetermined number of previously generated images to generate the threshold intensity. Determining the threshold intensity based on a plurality of images rather than based on just the image currently being enhanced can help avoid sharp changes from one enhanced image to the next, which may be particularly useful for video frame enhancement.

In some examples, the threshold intensity is determined periodically for a series of fluorescence images, with each periodically determined threshold intensity being used for multiple images. For example, the threshold intensity can be determined for every other fluorescence image in a series of fluorescence images and a determined threshold intensity can be used as the threshold for two sequential images. This can decrease the computational costs since threshold intensities do not need to be computed for each image in the series.

Returning to step 104, in some examples, values that are below the threshold intensity value are reduced according to a transfer function. The transfer function may be designed to suppress the appearance of background fluorescence emission by decreasing values according to how far below the values are from the threshold intensity. For example, values that are closer to the threshold intensity may be decreased to a greater degree than values that are further from the threshold intensity.

In some examples, the transfer function for adjusting the intensity values is configured so that the peak response in the image is minimally affected (or altogether unaffected). The transfer function can be configured so that the brightest areas in any given image are displayed with a similar brightness as they appear in the un-enhanced image. This can ensure that when panning across a scene, regions with no targeted tissue (or at least not having targeted imaging agent) will look dimmer than regions with targeted tissue, and scenes with higher concentration of targeted imaging agent will look brighter than those with lower concentrations.

In some examples, the transfer function is a continuous function so that small changes in intensity level do not produce noticeable step changes in the enhanced image. As such, a change between consecutive brightness levels in the un-enhanced image does not result in a display in the enhanced image that implies a fundamental difference in the nature of the tissue.

The transfer function can be a differentiable function. While discontinuities in the derivative of a transfer function are generally less noticeable than step changes in the brightness level, such discontinuities may still be perceptible as a contour-like effect that highlights an arbitrary signal level. As such, the transfer function may be configured so that a small difference in the un-enhanced intensities, whether up or down from a given value, produce a similar difference in the enhanced intensities.

In some examples, the transfer function passes through the origin, such that there is no arbitrary cut-off to intensity values, which can ensure that no data is hidden from the user. By providing a transfer function that passes through the origin, background regions of the image (those associated with non-targeted regions of tissue) are suppressed but not masked.

In some examples, the transfer function is a nonlinear function, such as a power function having the form, $$f(x)=ax^p$$

where x is an intensity value in the original fluorescence image and f(x) is the corresponding intensity value in the enhanced image. The power factor p is a predetermined value that controls the amount of suppression of values below the predetermined threshold. The power factor can be any suitable value, with higher values resulting in greater suppression. The power factor can be greater than one, at least 1.4, at least 1.6, at least 1.8, at least 2, at least 2.5, at least 3, or at least 5. The power factor can be less than 10, less than 8, less than 5, less than 3, or less than 2.5.

Parameter a is a scaling factor that can be used to scale the intensities in the enhanced image. In some examples, the scaling factor is selected so that a given value in the fluorescence image, such as a maximum value or other predetermined value, is the same in the enhanced image. In some examples, the scaling factor can be a function of the threshold intensity and/or the power factor. In some examples, the scaling factor is set such that values in the fluorescence image that are equal to the threshold intensity remain the same in the enhanced fluorescence image. For example, the scaling factor a can be defined as, $$a=\frac{1}{T^p-1}$$

where T is the threshold intensity.

In some examples, the transfer function may be an approximation of a non-linear function, such as a non-linear function approximated by a function comprising one or more linear segments. The one or more linear segments may be short in length so that the approximation closely resembles the non-linear function and has a substantially similar effect in generating the enhanced image.

In some examples, such as those using the power function discussed above, the amount of reduction of a given intensity value is based on a magnitude of the intensity value. Higher values have a greater reduction relative to lower values. By reducing higher values—values that are closer to, but still below, the threshold intensity—to a greater degree, the contrast between values near but below the threshold intensity and values at or above the threshold intensity can be greatly enhanced.

In some examples, intensity values that are at or above the threshold intensity are also adjusted according to the same non-linear function used to adjust the intensity values that are below the threshold intensity. While this results in intensity values that are above the threshold intensity being increased in the enhanced image, the threshold intensity can be selected so that there are relatively few intensities that are adjusted higher.

In some examples, intensity values that are at or above the threshold intensity remain unmodified in the enhanced fluorescence image. In some examples, intensity values that are at or above the threshold intensity are adjusted according to a different function than that used for reducing the intensity values that are below the threshold intensity. For example, a function with a constant slope may be used to adjust the intensity values that are above the threshold intensity. In some examples, the slope may be equal to the slope of the power function at the threshold intensity.

At step 106, the enhanced fluorescence image is displayed. The enhanced fluorescence image can be displayed on a display screen during the imaging session, such as intra-operatively in the operating room to assist a surgeon in identifying the target tissue. For example, the target tissue may be a tumor, a surgeon can use a fluorescence imager, such as an open field imager or an endoscopic imager, to generate an image of the area of the body that may include the tumor, and the enhanced image can be displayed to the surgeon to assist the surgeon in locating the tumor for removal. In some examples, the enhanced image can be displayed after the imaging session in which the un-enhanced image was generated has completed, such as for research and/or diagnosis.

The enhanced fluorescence image may be displayed by itself and/or may be combined with one or more other images. In some examples, the enhanced fluorescence image is displayed in combination with a visible light image, such as a white-light image. The enhanced fluorescence image can be displayed as an overlay on the visible light image, can be displayed picture-in-picture, or can be displayed side-by-side with the visible light image. In some examples, the enhanced fluorescence image is displayed in more than one of these ways at the same time.

Method 100 can be used for single fluorescence images and can be used for time-series of fluorescence images. For example, method 100 can be used on each frame of a series of video frames so that the video displayed on the display screen is a video in which the contrast has been enhanced according to the principles described above. In some examples, the enhanced fluorescence images are displayed in real-time—i.e., as the images are generated by the imager—so that a surgeon can be accurately guided by the enhanced fluorescence images.

In some examples, method 100 includes illuminating the tissue with fluorescence excitation light for causing the fluorescence agent to fluoresce. In some examples, method 100 includes capturing the fluorescence emission from the fluorescing agent with a fluorescence imager and enhancing the image generated from the imager according to the steps described above. In some examples, the fluorescence imager is an endoscopic imager that images tissue within a surgical cavity. The endoscopic imager may be pre-inserted into the surgical cavity prior to imaging the tissue. In some examples, the fluorescence imager is an open field imager that may be a platform mounted imager or a handheld imager.

In some examples, the fluorescence image generated by the imager comprises an intensity value for each pixel in the imager. In some examples, the fluorescence image is based on an image generated by the fluorescence imager. For example, one or more processing steps may be performed between the generation of the fluorescence image by the fluorescence imager and the performance of step 102 of method 100. Examples of such processing steps include scaling, trimming, denoising, and normalizing. Accordingly, In some examples, the number of intensity values in the fluorescence image that is received at step 102 may be different than the number of pixels of the imager that generated the image from which the received fluorescence image was derived. In some examples, one or more image processing steps may be performed after the fluorescence image is received at step 102. For example, generating the enhanced fluorescence image may include one or more of a scaling step, a trimming step, a denoising step, and a normalizing step.

In some examples, the fluorescence agent that is preferentially accumulated or activated in a target region in the tissue and the fluorescence agent that is not located within the target region in the tissue are the same fluorescence agent. For example, the fluorescence agent may be configured to target tumor cells, and a portion of the fluorescence agent may have accumulated in the target tumor while another portion of the fluorescence agent may be present in other tissue, which may be due to the blood that transports the fluorescence agent perfusing the other tissue. In some examples, at least some of the fluorescence emission from areas that are not located within the target region in the tissue is from a different fluorescence agent and/or from autofluorescence.

In some examples, a denoising step is performed on the fluorescence image prior to generating the enhanced fluorescence image. In examples in which the threshold intensity is determined dynamically, the denoising step can be performed either before or after the threshold intensity is determined. The denoising step can smooth images before contrast enhancement and can also remove small singular noisy areas, which can be areas that are unusually brighter than surrounding areas and can result from external light reflectance, sensor noise, and other well-known sources.

In some examples, a denoising step performed prior to generating the enhanced image includes applying an average filter on an image I to obtain a smoother version I'. Once the smoother version I' is obtained, a variation ratio for each pixel is calculated as:

$$\text{Ratio}(x, y) = \frac{|I(x, y) - I'(x, y)|}{I(x, y)}$$

If Ratio(x,y)≥0.5, the corresponding pixel I(x,y) is treated as a singular pixel and is set to zero. After that, a second average filter is applied on the non-singular values in to smooth the discontinuities, resulting in a denoised image.

In some examples, values in the denoised image may be reduced according to the principles discussed above. In some examples, the threshold intensity is determined based on the denoised image. In other examples, the threshold intensity is determined prior to the denoising step.

In some examples, method 100 may be repeated for each image in a time series of fluorescence images. For example, a series of video frames may be generated in real-time during a surgical procedure to assist a clinician in visualizing the tissue in the imaging field, and method 100 may be performed on each video frame as the frames are generated. Enhanced fluorescence images may be generated and displayed as an enhanced video on a display screen to assist the clinician in locating and visualizing the target region of tissue.

Figure 2A:
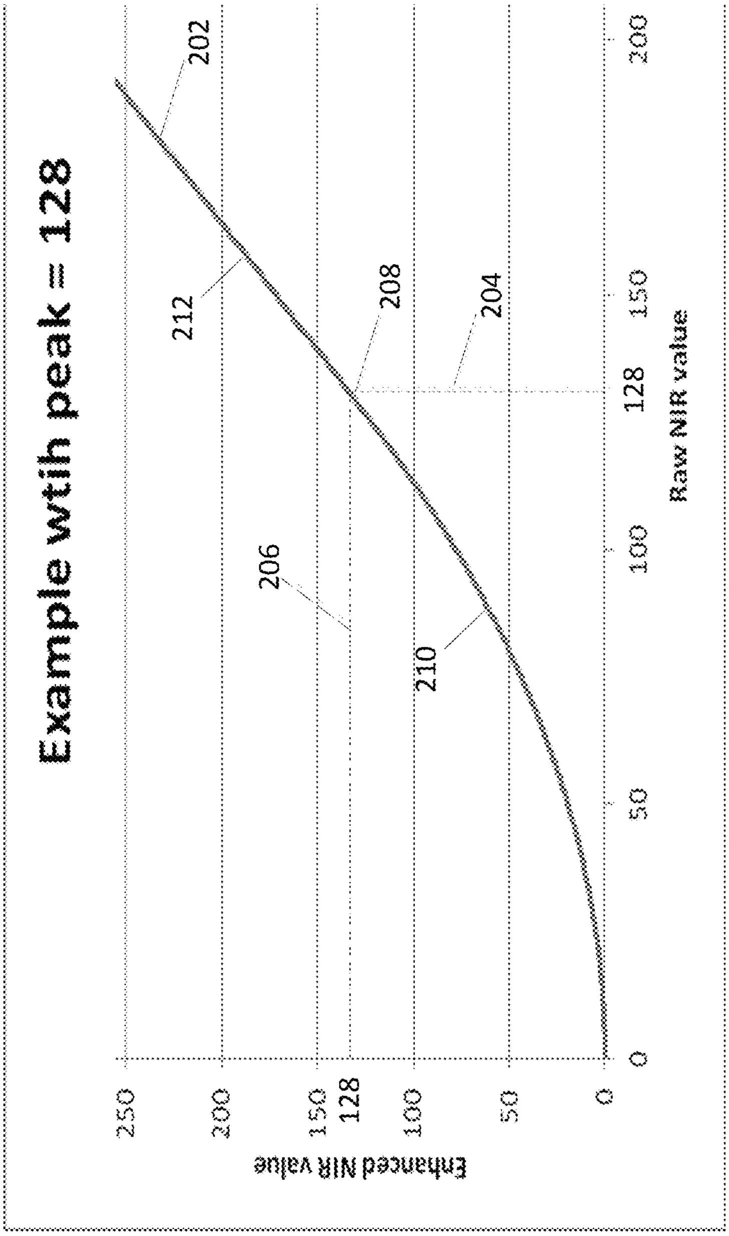
FIGS. 2A and 2B illustrate exemplary transforms for enhancing a fluorescence image.
Figure 2B:
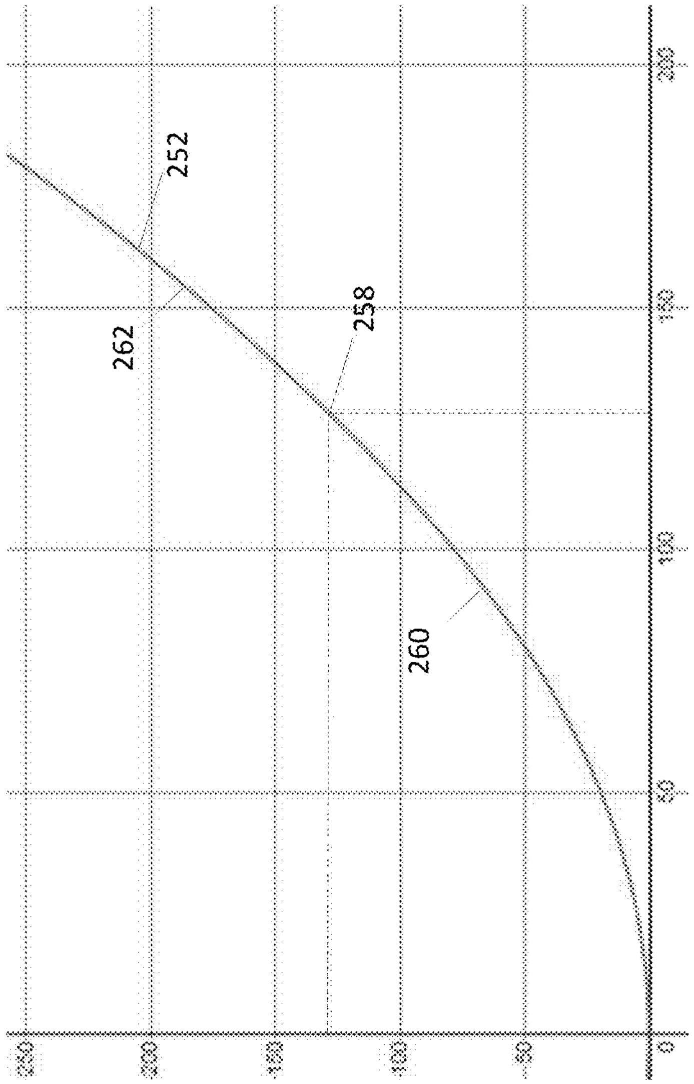

FIGS. 2A and 2B illustrate exemplary transforms for generating an enhanced fluorescence image from an un-enhanced fluorescence image, according to method 100. In each figure, the x-axis is associated with the un-enhanced fluorescence image intensity values and the y-axis is associated with the corresponding enhanced florescence image values. The curves 202 and 252 show the mapping of the un-enhanced values to the enhanced values.

In the example shown in FIG. 2A, the curve 202 is scaled so that a value of 128 on the x-axis is mapped to a value of 128 on the y-axis. This curve 202 could be used, for example, for generating an enhanced image in which the threshold intensity is 128 and values below this threshold are reduced according to the curve 202. A power function defines the lower portion 210 of the curve 202—for transforming intensities that are below the threshold intensity 208. The power of the power function in this example is equal to 2. The scaling factor for the power function is based on the power and the threshold intensity 208 so that, in this example, intensity values equal to the threshold intensity will remain the same in an enhanced image generated using curve 202, as shown by lines 204 and 206. A constant slope function defines the upper portion 212 of the curve 202 and is used to transform intensity values that are above the threshold intensity 208. The slope of the upper portion 212 of the curve 202 is equal to the slope of the lower portion 210 of the curve 202 at the threshold intensity 208.

The curve 252 of FIG. 2B is similar to the curve 202 of FIG. 2A except that the same power function used for the lower portion 260 is also used for the upper portion 262. Therefore, relative to curve 202, intensity values that are above the threshold intensity 258 will be increased to a greater degree since the slope of the power function is ever-increasing.

Figure 3:
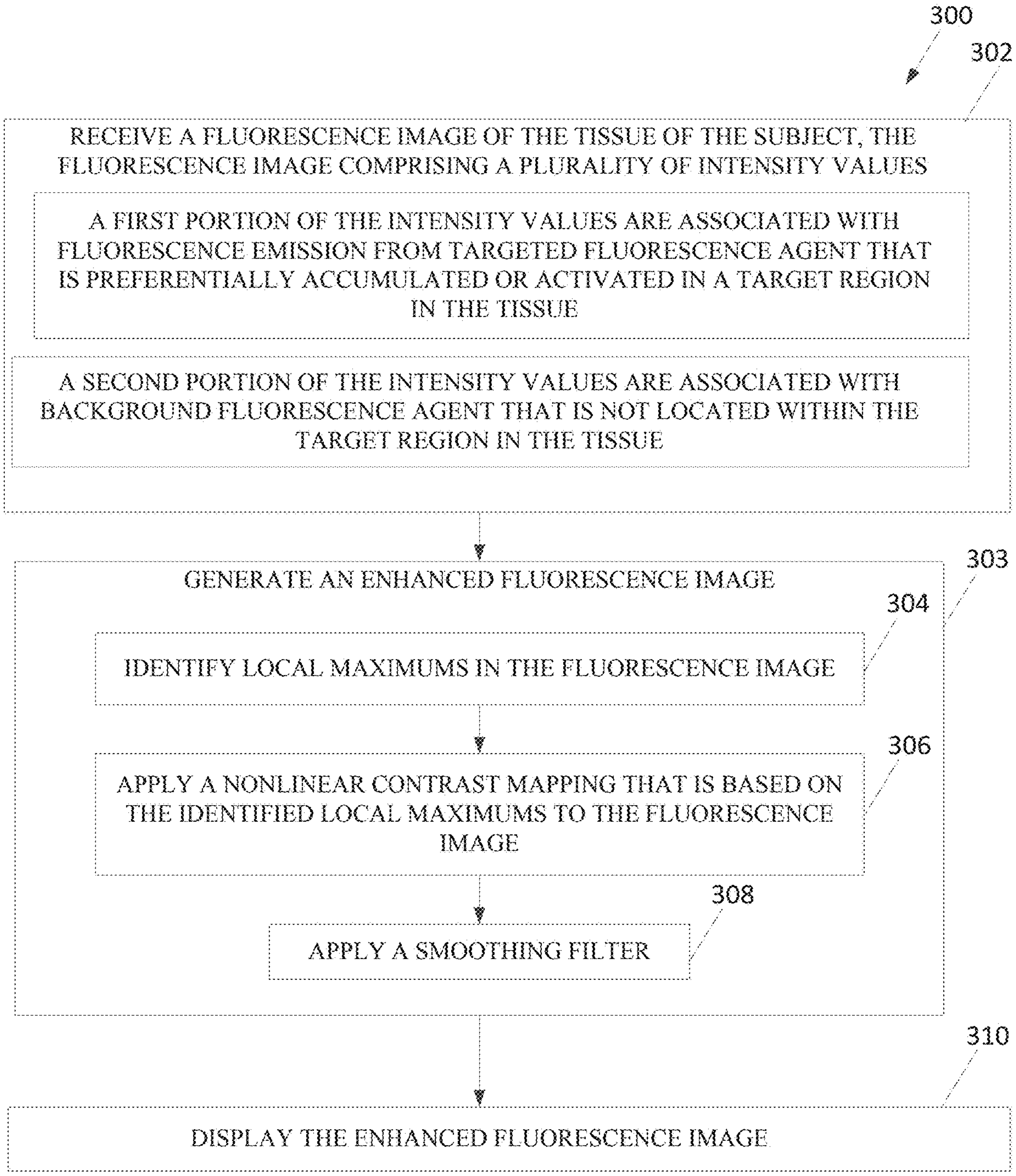
FIG. 3 illustrates an exemplary method for enhancing the contrast in a fluorescence image that captures a targeted fluorescence agent.

FIG. 3 illustrates a method 300 for enhancing the contrast in a fluorescence image that captures a targeted fluorescence agent, according to another example. Method 300 includes a nonlinear contrast mapping transform for transforming un-enhanced intensity values to enhanced intensity values based on a distance transform. The transform is designed to enhance the contrast in fluorescent images, highlight the brightest area and suppress the rest as background. As long as the desired targets are the areas of brightest fluorescence, the fluorescence from targets will be enhanced in the displayed image.

At step 302, a fluorescence image is received. This step is similar to step 102 of method 100, and therefore, further description of this step is omitted. At step 303, an enhanced fluorescence image is generated according to steps 304-308 as described in the following.

At step 304, local maximums in the fluorescence image are identified for enhancement. Given a M×N fluorescent image I, the maximum intensity value $I_M$ is located. With the predefined local maximum threshold τ (this can be defined as a percentage, such as 90%, 95%, 98%, etc.), the locations $\{(x_i,y_i)\}_{i\in LM}$ of all the pixels in local maximum set LM are obtained, according to:

$$I(x_i, y_i) \geq \tau \cdot I_M$$

In some examples, to reduce the computational cost, non-maximum suppression is applied to refine these local maximum points within the neighborhood. Alternatively, In some examples, clustering is used to find centroids if multiple local maximum points are located in a neighborhood.

At step 306, a nonlinear contrast mapping that is based on the local maximums identified in step 304 and a distance transform is applied to the fluorescent image, as follows. For each pixel $I_{old}(x,y)$ in fluorescent image I, the following nonlinear transform is applied on its intensity value to obtain the mapped value $I_{new}(x,y)$.

$$I_{new}(x, y) = \max\left(\frac{I_{old}(x, y)\cdot I_{upper}}{I(x_i, y_i)\cdot \exp\frac{\|(x,y)-(x_i,y_i)\|}{\sigma^2}}\right)_{i\in LM}$$

$\sigma^2$ is the scale of Gaussian kernel and can be used to tune the mapping tail in the enhanced image. $I_{upper}$ is the upper bound intensity value mapped in the enhanced image. $I_{upper}$ is set as follows:

$$I_{upper} = \begin{cases} 255 & \text{if ratio} \geq 2 \\ \dfrac{128}{\exp\frac{(ratio-2)^2}{\omega^2}} & \text{if ratio} < 2 \end{cases}$$

The default value of kernel scale $\omega^2$ can be set to 0.1, and the ratio is a parameter that is used to assess if there is sufficient contrast in the un-enhanced image to enable contrast to be meaningfully enhanced. The values of 255 and 128 are for 8-bit intensity values and can be adjusted accordingly for smaller or larger pixel value sizes. The ratio can be calculated based on following equation:

$$\text{ratio} = \frac{\bar{I}_M}{\bar{I}_{Valid}}$$

$\bar{I}_M$ is the average intensity value of all the local maximum pixels without non-maximum suppression. $\bar{I}_{Valid}$ is the average intensity value of all the valid pixels. Valid pixels are defined as those pixels with a signal intensity value equal to or greater than 10 intensity levels. Pixels with an intensity value below 10 intensity levels are considered noise. The ratio value of 2 is an exemplary value that was determined empirically based on a test set of images with tumors and negative counter-examples and can be a different value for different examples.

At step 308, generation of the enhanced image is completed by applying a smoothing filter to the mapped results $I_{new}(x,y)$ to remove any singular mapping point. The smoothing filter can be, for example, a low pass Gaussian filter.

At step 310, the enhanced image is displayed. This step is similar to step 106 of method 100, and therefore, further description of this step is omitted.

Figure 4B:
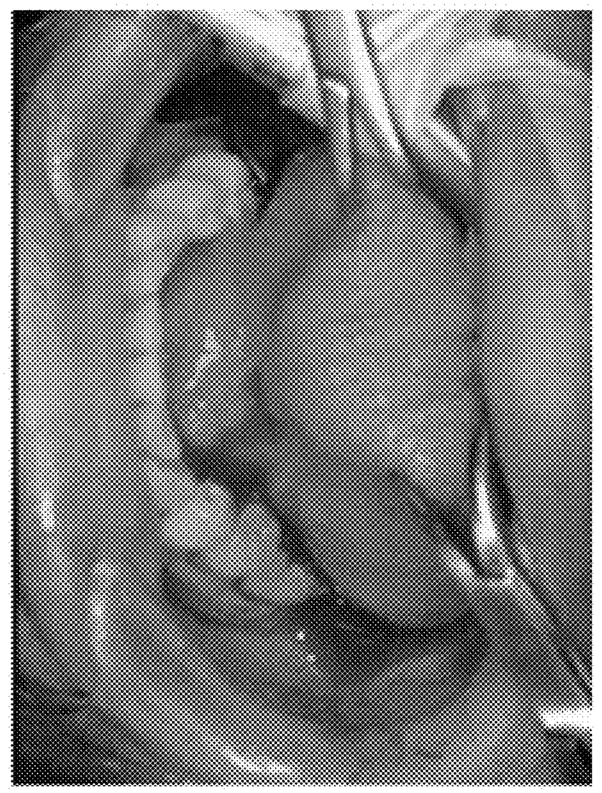
FIG. 4B is an example of a false color overlay of the fluorescence image of FIG. 4A on a white light image of the tissue of the subject.
Figure 4A:
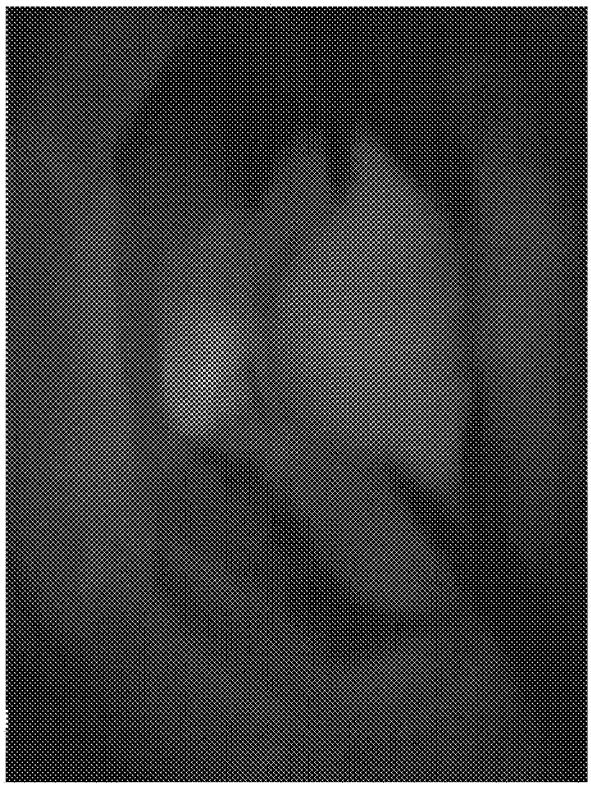
FIG. 4A is an example of an unenhanced fluorescence image of a targeted agent in tissue of a subject.
Figure 4D:
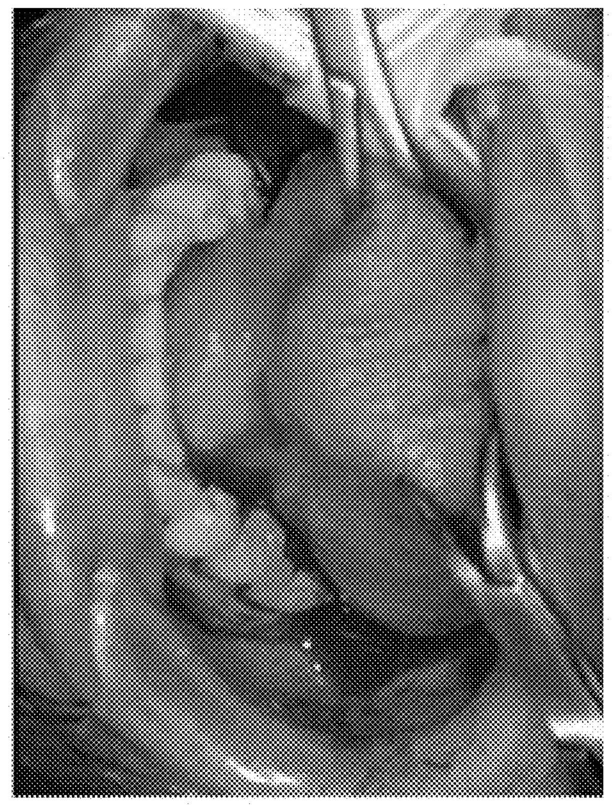
FIG. 4D is an example of a false color overlay of the enhanced fluorescence image of FIG. 4C on the white light image of the tissue of the subject.

FIGS. 4A-4D illustrate results of performing method 300 on an exemplary fluorescence image to generate an enhanced image. FIG. 4A illustrates the un-enhanced fluorescence image of tissue of a subject. The fluorescence image is a grayscale image with pixels that have higher intensity being shown in lighter shades. FIG. 4B is a false color overlay of the un-enhanced fluorescence image on a white light image of the tissue of the subject that was generated at approximately the same time as the fluorescence image. Fluorescence emission captured in the fluorescence image is shown in green in the overlay of FIG. 4B. An area of higher intensity can be seen in the center of the image, underneath the tongue, which indicates targeted tissue, such as a tumor. Other areas within the image, such as the tongue and lips also show a degree of fluorescence due to the fluorescence agent being carried in blood perfusing those areas—this can be regarded as background fluorescence that is to be suppressed in the enhanced image. The amount of background fluorescence in the un-enhanced fluorescence image makes the targeted tissue beneath the tongue somewhat difficult to clearly see.

Figure 4C:
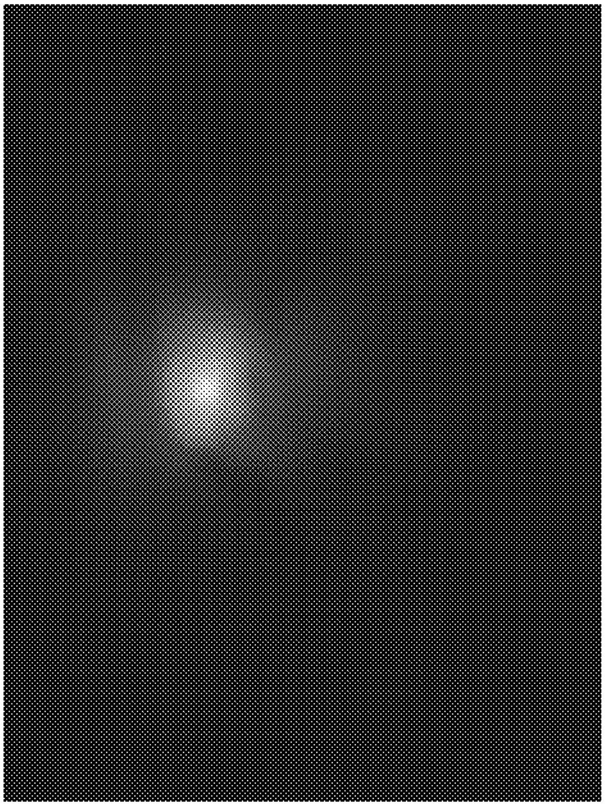
FIG. 4C is an example of an enhanced fluorescence image generated from the fluorescence image of FIG. 4A using the method of FIG. 3.

FIG. 4C illustrates the enhanced fluorescence image generated from the un-enhanced fluorescence image according to method 300. The brightness of areas other than the brightest portion in the middle of the image has been suppressed. The enhanced fluorescence image is displayed as an overlay on a white light image in FIG. 4D. Comparing the overlay of FIG. 4D to the overlay of FIG. 4B, it is apparent that the background fluorescence has been substantially suppressed such that the target tissue located beneath the tongue is clearly distinguishable from surrounding tissue.

Figure 5:
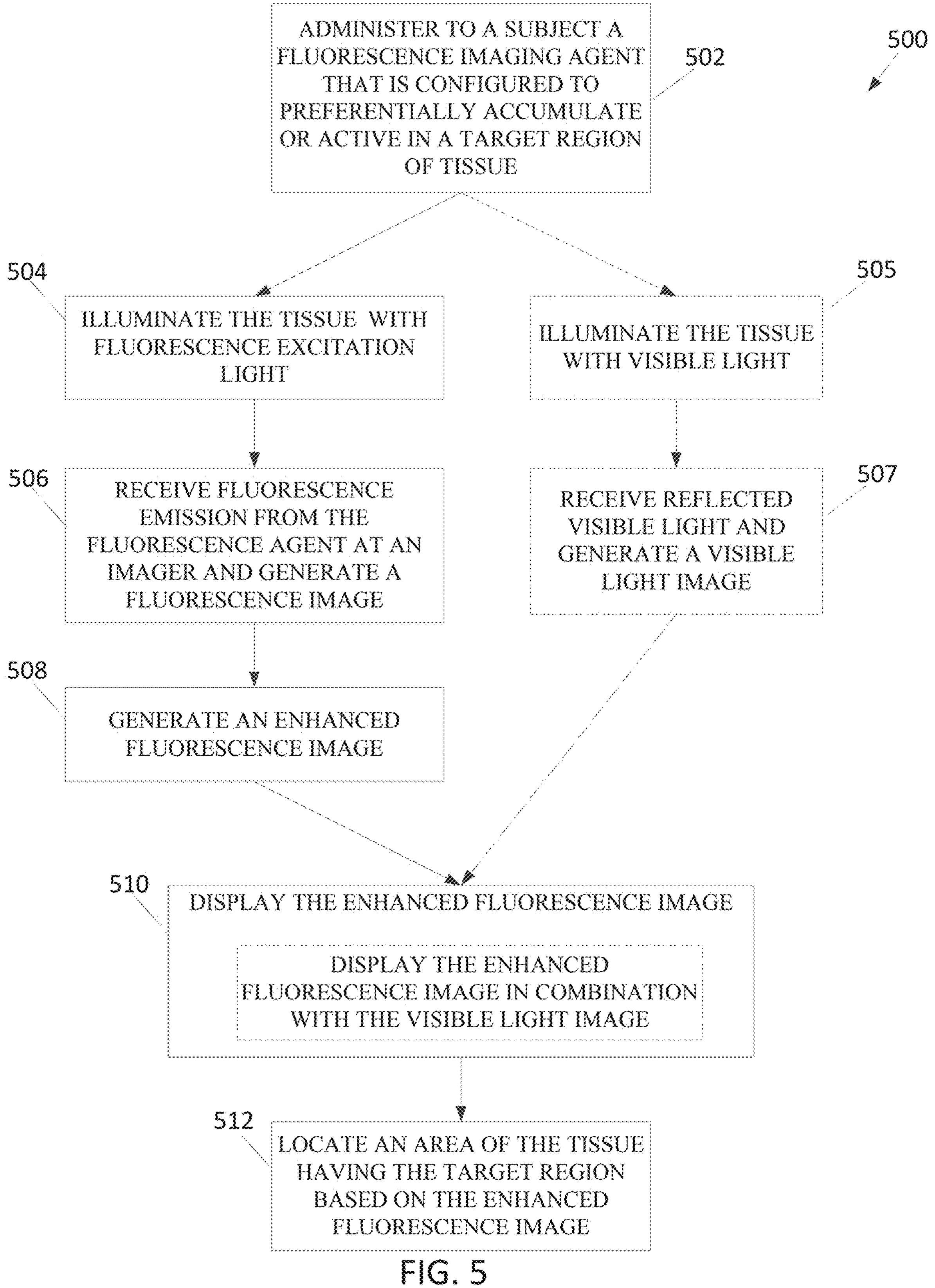
FIG. 5 illustrates an exemplary method for locating a target region of tissue based on an enhanced fluorescence image.

FIG. 5 illustrates a method 500 for locating a target region of tissue based on enhancing fluorescence images in accordance with the methods and systems described above. At step 502, one or more fluorescence imaging agents are administered to the subject. At least one of the fluorescence imaging agents is configured to target a particular region of tissue. For example, at least one imaging agent may be configured to bind to tumor cells. In some examples, the fluorescence imaging agent (e.g., indocyanine green ("ICG")) may be administered to the subject (e.g., into a vein, an artery, or other tissue) as a bolus injection, in a suitable concentration for imaging. In some examples in which multiple fluorescence imaging agents are used, such agents may be administered simultaneously (e.g., in a single bolus), or sequentially (e.g., in separate boluses). In some examples, the fluorescence imaging agent may be administered by a catheter. In some examples, the fluorescence imaging agent may be administered to the subject less than an hour in advance of generating fluorescence images of tissue containing the fluorescence imaging agent. For example, the fluorescence imaging agent may be administered to the subject less than 30 minutes prior to imaging. In other examples, the fluorescence imaging agent may be administered at least 30 seconds in advance of imaging. In some examples, the fluorescence imaging agent may be administered contemporaneously with imaging. The method of visualizing tissue of the subject can exclude the step of administering the fluorescence imaging agent.

At step 504, the tissue of the subject is illuminated with a fluorescence excitation light having a suitable intensity and a suitable wavelength for exciting the fluorescence imaging agent configured for targeting the particular region of tissue. In some examples, the tissue is illuminated with visible light at step 505 for generating a visible light image.

At step 506, fluorescence emission from the fluorescence agent present in the imaging field of view is received at an imager. The imager can be, for example, an endoscopic imager or an open field imager. The imager can generate a fluorescence image based on the intensity of light received at pixels of the imager. In some examples, visible light reflected from the tissue is received at the imager and a visible light image is generated at step 507.

At step 508, an enhanced fluorescence image is generated from the fluorescence image generated at step 506 according to any of the methods described herein, including method 100 of FIG. 1 and method 300 of FIG. 3. At step 510, the enhanced fluorescence image is displayed for visualization by a clinician. In some examples, the enhanced fluorescence image is displayed in combination with a visible light image. For example, the enhanced fluorescence image may be displayed as an overlay of the visible light image.

At step 512, the clinician locates a target region of tissue based on the enhanced fluorescence image. The target region of tissue may be located for diagnosis or for treatment. For example, the target region of tissue may be located during a surgical procedure on the subject and the located region of tissue may be removed by a surgeon based on the surgeon's visualization of the target region of tissue via the enhanced fluorescence image.

In some examples, at least a portion of the methods described above, including methods 100 and 300, may be performed by a computer system located separate from a medical imaging system. For instance, some or all of the steps of receiving a fluorescence image, generating an enhanced fluorescence image, and displaying the enhanced fluorescence image, as included in methods 100 and 300, may be performed by a computer system at an off-site location that is remote from a clinical site (e.g., where a fluorescence imaging system is situated) or by a computer system that is located at a clinical setting but not embodied in an imaging system. In these examples, the fluorescence image(s) may be received as a result of a transfer of image data from a data storage medium (e.g., hard drive, cloud storage, etc.) or through a network communication (e.g., wired connection, Internet, wireless network based on a suitable wireless technology standard, etc.). For instance, a method may involve a client-server architecture, such that an imaging system may include client hardware that sends image data to a computing server and loads processed data (e.g., ranking map image or interim outputs of various steps of the methods described herein) back onto the imaging system. After the client hardware in the imaging system loads the processed data, the imaging system may further process the data and/or display the processed data in accordance with the methods described herein.

In some examples, at least a portion of the method is performed by one or more processors at a computer system incorporated into a medical imaging system, such as at a clinical site. For example, some or all of the steps of receiving a fluorescence image, generating an enhanced fluorescence image, and displaying the enhanced fluorescence image, as included in methods 100 and 300, may be performed by a computer system in a medical imaging system. In some of these examples, the method may further include generating the fluorescence image prior to receiving the fluorescence image, as described in method 500.

Although various exemplary variations are described herein in the context of fluorescence images, the methods may be applied to other sources of images that relate to the preferential accumulation or activation of an imaging agent in a target region of tissue, and for other clinical purposes. For example, the images may be derived from computerized tomographic (CT) angiography with a radio-opaque contrast dye. As another example, the images may be derived from positron emission tomography (PET) using a fluorodeoxyglucose (FDG) or other radiotracer to evaluate metabolic activity and potentially assess pathology and/or provide information usable for assessing pathology. As another example, the images may be derived from contrast-enhanced ultrasound imaging employing the use of gas-filled microbubble contrast medium administered intravenously to the systemic circulation. Such ultrasonic imaging using microbubble contrast agents enhances the ultrasound backscatter or reflection of the ultrasound waves to produce a unique sonogram with increased contrast due to the high echogenicity (i.e., ability of an object to reflect the ultrasound waves) difference between the gas in the microbubbles and the soft tissue. Although reference is made in the specification to a fluorescence agent or a fluorescence dye, suitable imaging agents other than fluorescence agents or dyes may be used depending on the type of imaging technology being employed to generate the time series of images in variations where the time series of images and/or the subject time series of images is not fluorescence-based.

Systems for Displaying Enhanced Florescence Images of a Target

Figure 6:
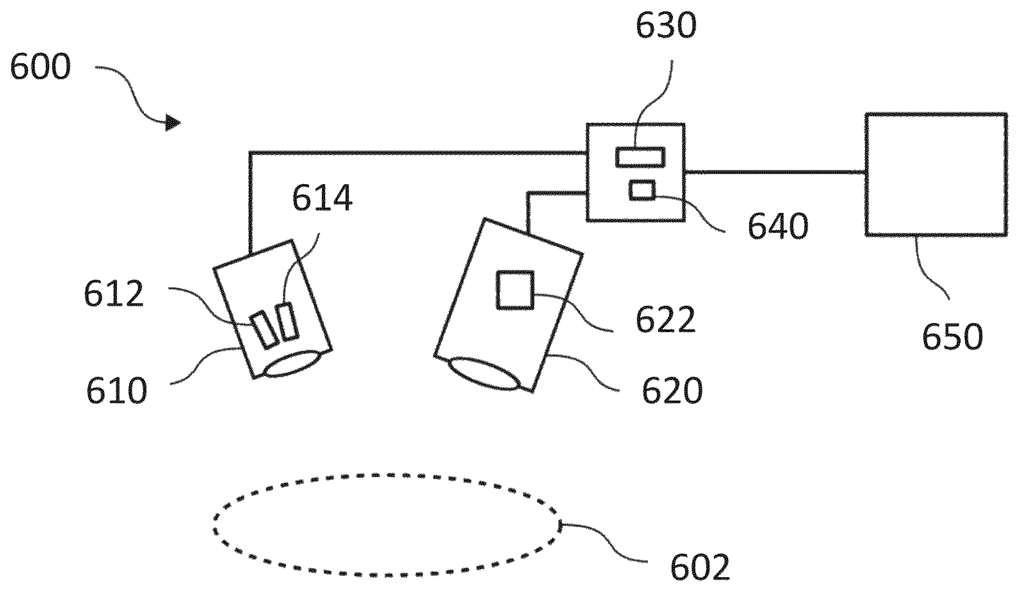
FIG. 6 is an illustrative depiction of an exemplary imaging system for fluorescence imaging of tissue of a subject.

A system for visualizing a target region of tissue based on enhanced fluorescence images, according to some variations, includes an imaging system for acquiring one or more images or time series of images of tissue (e.g., one or more time series of visible light images, one or more time series of fluorescence images, one or more time series of x-ray images, one or more time series of ultrasonic images, etc.), and one or more processors and memory having instructions stored thereon, wherein the instructions when executed by the one or more processors cause the system to perform the methods substantially as described above for characterizing tissue and/or predicting the clinical data. FIG. 6 illustrates an exemplary imaging system 600 for imaging tissue 602 that includes a target region that can be visualized using the methods described above. In some examples, system 600 include an image acquisition assembly 620 (also referred to herein as an imager) having at least one image sensor 622 configured to acquire an image or a sequence of video frames depicting the tissue and/or one or more features of the tissue, and a processor 630.

Figure 7:
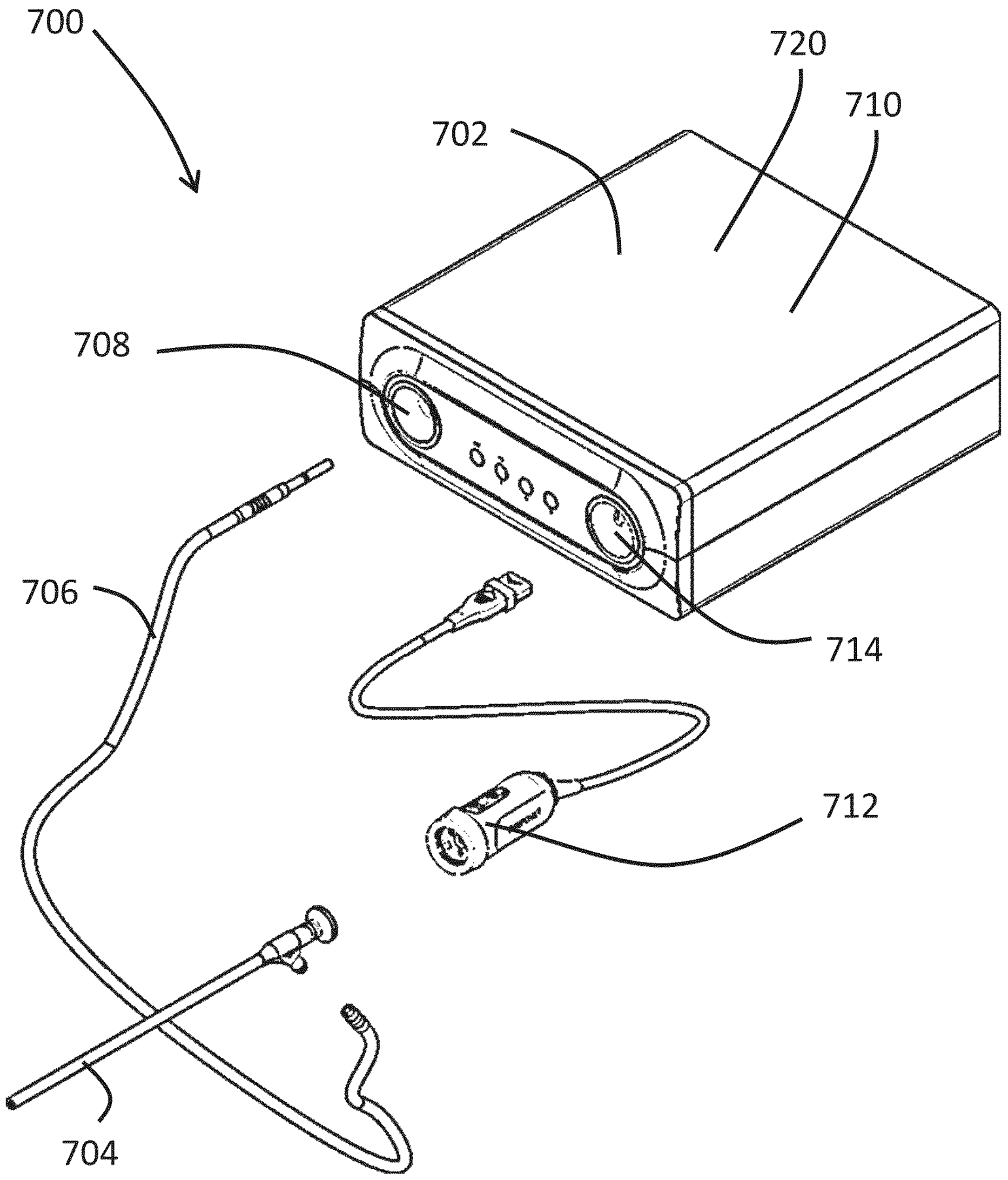
FIG. 7 illustrates an example of an endoscopic imaging system.

In some variations, at least part of the imaging system may be embodied in an endoscopic imaging system, such as for minimally-invasive procedures. For example, as shown in FIG. 7, an endoscopic imaging system 700 may include an illuminator 702 with a light source assembly configured to provide visible light and/or fluorescence excitation light to a surgical laparoscope 704 via a light guide 706 that is connected to the illuminator 702 via a light guide port 708. A processor 710 and/or controller 720 may, in some variations, be within the same housing as the illuminator 702, as shown in FIG. 7, and may be configured to perform at least some of the aspects of any of the methods described herein, including methods 100, 300, and 500 described above. An image acquisition assembly 712 may receive signals via connection to the endoscope 704, and may pass acquired images to the processor 710 via connection to the processor 710 such as through port 714. Certain aspects of the light source assembly, image acquisition assembly, processor, and/or controller may be similar to those described in more detail below.

Light Source Assembly

As shown in the schematic of FIG. 6, the imaging system 600 may include a light source assembly 610 including a visible light source 612 that emits visible light (e.g., full spectrum visible light, narrow band visible light, or other portions of the visible light spectrum) and/or an excitation light source 614 that emits excitation light for exciting fluorophores in the tissue 602 and causing fluorescence emission.

The visible light source 612 is configured to emit visible light for illumination of the object to be imaged. In some variations, the visible light source may include one or more solid state emitters, such as LEDs and/or laser diodes. For example, the visible light source may include blue, green, and red (or other color components) LEDs or laser diodes that in combination generate white light illumination. These color component light sources may be centered around the same wavelengths around which the image acquisition assembly (described further below) is centered. For example, in variations in which the image acquisition assembly includes a single chip, single color image sensor having an RGB color filter array deposited on its pixels, the red, green, and blue light sources may be centered around the same wavelengths around which the RGB color filter array is centered. As another example, in variations in which the image acquisition assembly includes a three-chip, three-sensor (RGB) color camera system, the red, green, and blue light sources may be centered around the same wavelengths around which the red, green, and blue image sensors are centered.

The excitation light source 614 is configured to emit excitation light suitable for exciting intrinsic fluorophores and/or extrinsic fluorophores (e.g., a fluorescence imaging agent introduced into the object) located in the object being imaged. The excitation light source 614 may include, for example, one or more LEDs, laser diodes, arc lamps, and/or illuminating technologies of sufficient intensity and appropriate wavelength to excite the fluorophores located in the object being imaged. For example, the excitation light source may be configured to emit light in the near-infrared (NIR) waveband (such as, for example, approximately 805 nm light), though other excitation light wavelengths may be appropriate depending on the application.

Figure 8:
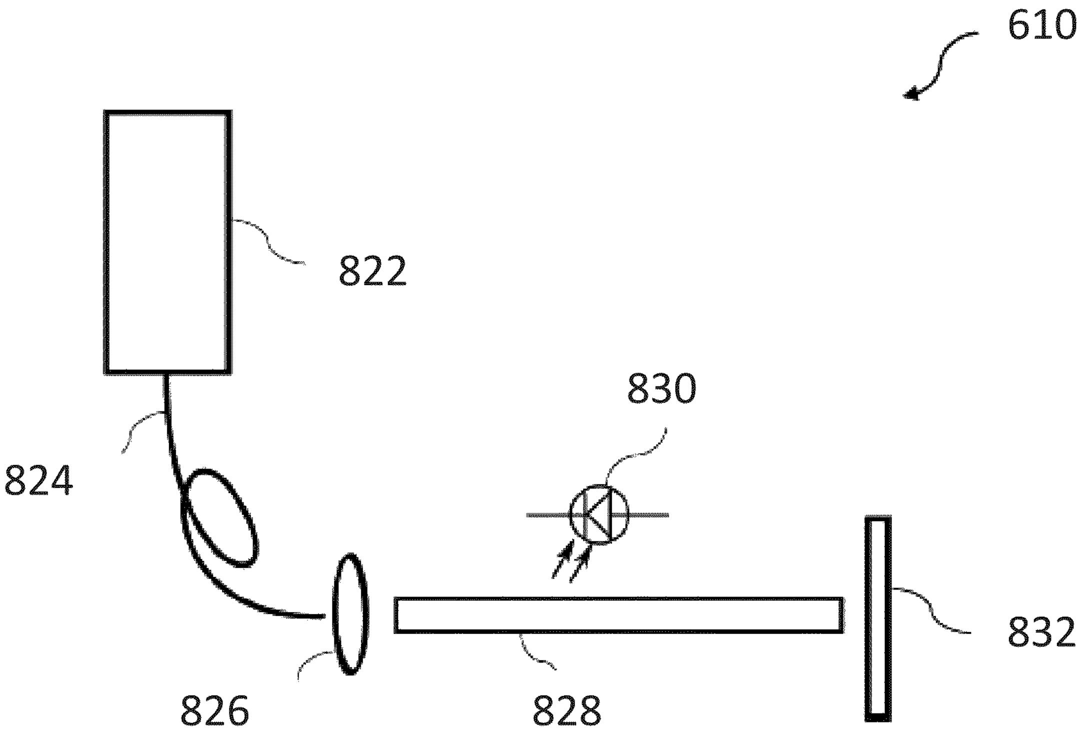
FIG. 8 is an illustrative depiction of an exemplary illumination module of an imaging system.

The light source assembly 610 may further include one or more optical elements that shape and/or guide the light output from the visible light source 612 and/or excitation light source 614. The optical components may include one or more lenses, mirrors (e.g., dichroic mirrors), light guides and/or diffractive elements, e.g., so as to help ensure a flat field over substantially the entire field of view of the image acquisition assembly 620. For example, as shown in the schematic of FIG. 8, the output 824 from a laser diode 822 (providing visible light or excitation light) may be passed through one or more focusing lenses 826, and then through a light guide 828. The light may be further passed through an optical diffractive element 832 (e.g., one or more optical diffusers). Power to the laser diode 822 may be provided by, for example, a high-current laser driver and may optionally be operated in a pulsed mode during the image acquisition process according to a timing scheme. An optical sensor such as a solid state photodiode 830 may be incorporated into the light source assembly and may sample the illumination intensity produced by one or more of the light sources, via scattered or diffuse reflections from the various optical elements.

Image Acquisition Assembly

Figure 9:
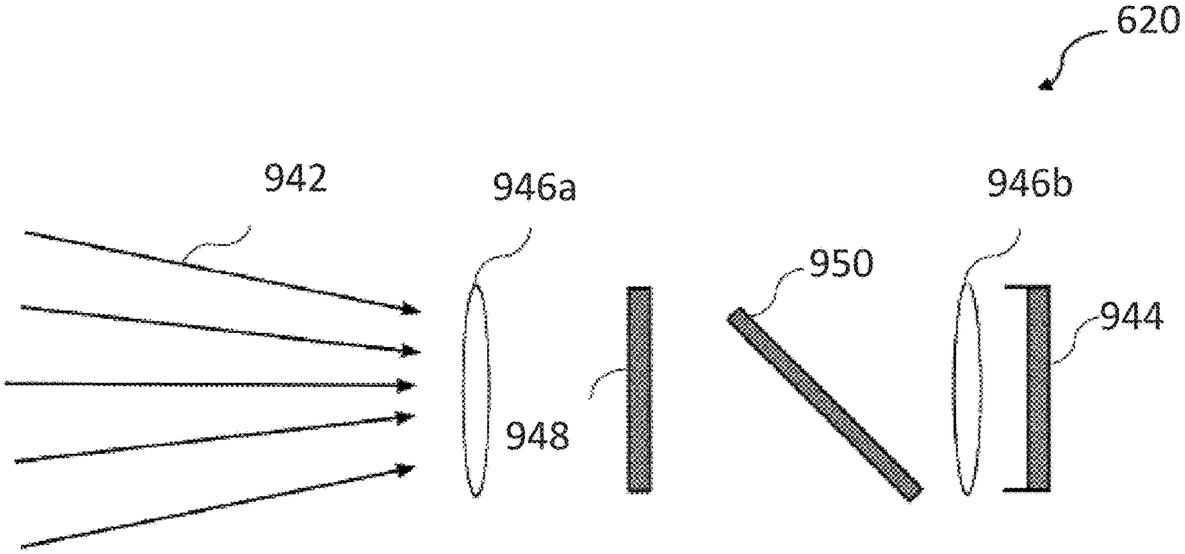
FIG. 9 is an exemplary camera module of an imaging system for imaging tissue of a subject.

The image acquisition assembly 620 may acquire reflected light video frames based on visible light that has reflected from the object, and/or fluorescence video frames based on fluorescence emitted by fluorophores in the object that are excited by the fluorescence excitation light. As shown in FIG. 9, the image acquisition assembly 620 may acquire images using a system of optics (e.g., one or more lenses 946*a*, one or more filters 948, one or more mirrors 950, beam splitters, etc.) to collect and focus reflected light and/or fluorescent light 942 onto an image sensor assembly 944. The image sensor assembly 944 may include at least one solid state image sensor. The one or more image sensors may include, for example, a charge coupled device (CCD), a CMOS sensor, a CID, or other suitable sensor technology. In one variation, the image sensor assembly 944 may include a single chip, single image sensor (e.g., a grayscale image sensor or a color image sensor having an RGB color filter array deposited on its pixels). In another variation, the image acquisition assembly may include a three-chip, three-sensor (RGB) image sensor assembly 944.

Processor and Controller

As shown in the schematic of FIG. 6, the system 600 may include a processor 630. The processor 630 may include, for example, a microprocessor or other suitable central processing unit. In particular, the processor 630 may be configured to execute instructions to perform aspects of the methods described herein. As visible light frames and/or fluorescence frames are acquired, at least a portion may be stored in a memory unit for record-keeping purposes and/or retrieval for analysis during other aspects of the method, as described below.

As shown in the schematic of FIG. 6, the system may include a controller 640, which may be embodied in, for example, a microprocessor and/or timing electronics. In some variations, a single image sensor may be used to acquire both visible light video frames and fluorescence frames, and the controller 640 may control a timing scheme for the visible light source and/or the excitation light source, and the image acquisition assembly. This timing scheme may enable separation of the image signal associated with the visible light signal and the image signal associated with the fluorescence signal. In particular, the timing scheme may involve illuminating the object with illumination light and/or excitation light according to a pulsing scheme, and processing the visible light image signal and fluorescence image signal with a processing scheme, wherein the processing scheme is synchronized and matched to the pulsing scheme (e.g., via a controller) to enable separation of the two image signals in a time-division multiplexed manner. Examples of such pulsing and image processing schemes have been described in U.S. Pat. No. 9,173,554, filed on Mar. 18, 2009 and titled "IMAGING SYSTEM FOR COMBINED FULL-COLOR REFLECTANCE AND NEAR-INFRARED IMAGING," the contents of which are incorporated in their entirety by this reference. However, other suitable pulsing and image processing schemes may be used to acquire reference video frames and low light video frames simultaneously, for example to acquire reflected light video frames and fluorescence video frames simultaneously. Furthermore, the controller may be configured to control the timing scheme for the visible light source and/or the excitation light source, and the image acquisition assembly based at least in part on the relative movement between the image acquisition assembly and the object.

Other Hardware

In some variations, the system may include image stabilizing technology that helps compensate for some ranges of motion (e.g., caused by unsteady hands holding the image acquisition assembly) in the acquired images. The image stabilizing technology may be implemented in hardware, such as with optical image stabilization technology that counteracts some relative movement between the image acquisition assembly and the object by varying the optical path to the image sensor (e.g., lens-based adjustments and/or sensor-based adjustments). Additionally, or alternatively, the image stabilization technology may be implemented in software, such as with digital image stabilization that counteracts some relative movement between the image acquisition assembly and the object (e.g., by shifting the electronic image between video frames, utilizing stabilization filters with pixel tracking, etc.). Such image stabilizing technology may, for example, help correct for motion blur in the characteristic low light video output (or in the acquired low light video frames) resulting from relative motion during long exposure periods.

The system may, in some variations, include one or more hardware motion sensors (e.g., gyroscope, accelerometer) that measure absolute motion of the image acquisition assembly. Information from these motion-measuring sensors may be used, in addition or as an alternative to the above-described motion-estimation algorithms, to determine which imaging mode of the system is suitable for a given set of circumstances.

Additionally, the system may include one or more data modules 850 that communicates and/or stores some or all of the acquired frames and/or information generated from the image data. For instance, the data module 850 may include a display (e.g., computer screen or other monitor), recorder or other data storage device, printer, and/or picture archiving and communication system (PACS). The system may additionally or alternatively include any suitable systems for communicating and/or storing images and image-related data.

A kit may include any part of the systems described herein, and/or the tangible non-transitory computer-readable medium described above having computer-executable (readable) program code embedded thereon that may provide instructions for causing one or more processors, when executing the instructions, to perform one or more of the methods described herein. For instance, the instructions may cause one or more processors, when executing the instructions, to perform an adaptive imaging method for generating low light video of an object. The method comprises receiving a sequence of low light video frames depicting the object, wherein the low light video frames are acquired by an image acquisition assembly; assessing relative movement between the image acquisition assembly and the object based on reference video frames comprising at least a portion of the low light video frames and/or a portion of a substantially simultaneously acquired sequence of higher light intensity video frames; adjusting a level of image processing of the low light video frames based at least in part on the relative movement between the image acquisition assembly and the object; and generating a characteristic low light video output from a quantity of low light video frames, wherein the quantity of the low light video frames is based on the adjusted level of image processing of the low light video frames. Furthermore, the kit may include instructions for use of at least some of its components (e.g., for installing the computer-executable (readable) program code with instructions embedded thereon, etc.).

Exemplary Imaging Agents

In some examples, a kit may include any part of the systems described herein and a fluorescence agent such as, for example, a fluorescence dye such as ICG or any suitable fluorescence agent or a combination of fluorescence agents. In some variations, a suitable fluorescence agent is an agent which can circulate with the blood (e.g., an agent which can circulate with, for example, a component of the blood such as plasma in the blood) and which fluoresces when exposed to appropriate excitation light energy. For example, ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other examples in which multiple fluorescence imaging agents are used, such agents may be administered simultaneously, e.g. in a single bolus, or sequentially in separate boluses. In some examples, the fluorescence imaging agent may be administered by a catheter. In certain examples, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other examples, the fluorescence imaging agent may be administered at least 30 seconds in advance of performing the measurement. In still other examples, the fluorescence imaging agent may be administered contemporaneously with performing the measurement. In some examples, the fluorescence imaging agent may be administered in various concentrations to achieve a desired circulating concentration in the blood. For example, in examples where the fluorescence imaging agent is ICG, it may be administered at a concentration of about 2.5 mg/mL to achieve a circulating concentration of about 5 μM to about 10 μM in blood. In various examples, the upper concentration limit for the administration of the fluorescence imaging agent is the concentration at which the fluorescence imaging agent becomes clinically toxic in circulating blood, and the lower concentration limit is the instrumental limit for acquiring the signal intensity data arising from the fluorescence imaging agent circulating with blood to detect the fluorescence imaging agent. In various other examples, the upper concentration limit for the administration of the fluorescence imaging agent is the concentration at which the fluorescence imaging agent becomes self-quenching. For example, the circulating concentration of ICG may range from about 2 μM to about 10 mM. Thus, in one aspect, the method comprises the step of administration of the imaging agent (e.g., a fluorescence imaging agent) to the subject and acquisition of the signal intensity data (e.g., video) prior to processing the signal intensity data according to the various examples. In another aspect, the method excludes any step of administering the imaging agent to the subject.

In some examples, a suitable fluorescence imaging agent for use in fluorescence imaging applications to generate fluorescence image data is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). In various examples, the fluorescence imaging agent comprises a fluorescence dye, an analogue thereof, a derivative thereof, or a combination of these. An example of the fluorescence agent is a fluorescence dye, which includes any non-toxic fluorescence dye. In certain variations, the fluorescence dye may include a dye that emits light in the near-infrared spectrum. In certain examples, the fluorescence dye may include a tricarbocyanine dye such as, for example, indocyanine green (ICG). In other variations, the fluorescence dye may comprise methylene blue, ICG or a combination thereof. In certain examples the dye is or comprises fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy5.5, etc.), IRDye800CW, CLR 1502 combined with a targeting ligand, OTL38 combined with a targeting ligand, or a combination thereof, which is excitable using excitation light wavelengths appropriate to each imaging agent. In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations in which some or all of the targeted and/or background fluorescence is derived from autofluorescence, one or more of the fluorophores or agents giving rise to the autofluorescence may be an endogenous tissue fluorophore (e.g., collagen, elastin, NADH, etc.), 5-aminolevulinic acid (5-ALA) or a derivative or product thereof, or a combination thereof. For example, 5-ALA may be converted in vivo to a product protoporphyrin IX which may emit fluorescence that may be imaged by the fluorescence imager.

In some examples, the fluorescence imaging agent is configured to target a region of tissue and is used for visualizing the targeted region. The following is an exemplary list of imaging agents that can be used according to various examples and the regions of tissue that they can target. ICG and/or Methylene blue may be used for targeting breast tissue, parathyroid tissue, and tumors. A proflavine agent can be used for targeting squamous cell neoplasia, Barrett's esophagus, colon polyps, dysplasia, anal dysplasia, head and neck cancer, cervical cancer, uterine cancer, oral disorders, and gastric cancer. ALA may be used for targeting gliomas, the bladder, and skin precancers and cancers. Hexaminolevulinate can be used for targeting the bladder, the cervix, and colorectal cancers. Methyl aminolevulinate can be used for targeting skin actinic keratosis, cancers, Bowen's disease, and acne. A cathepsin activatable can be used for targeting sarcomas, and colorectal, pancreatic, esophageal, breast, and prostate cancers. A protease activatable can be used for targeting breast cancer. Fluorescent lectin can be used for targeting colorectal cancer, neoplasms, and polyps. An HSP90 inhibitor can be used for targeting solid tumors. A chlorotoxin blocking chloride channels with Cy5.5 can be used for targeting gliomas, other CNS tumors, breast cancer, skin cancer, and sarcomas. A 7-aa peptide-IRDye800CW can be used for targeting gastrointestinal malignancies. A c-Met targeting peptide can be used for targeting colon cancer, esophageal cancer and high grade dysplasia, papillary thyroid cancer, and lung cancer. A folate receptor targeter can be used for targeting renal cell, lung, ovarian, pituitary, and pleural cancers. Tumor-specific integrin receptor binder can be used for targeting breast cancer. Anti-EGFR binding peptide can be used for targeting colon cancer and cholangiocarcinoma. Anti-EGFR affibody can be used for targeting gliomas, sarcomas, and head and neck cancers. GRPR receptor binding peptide can be used for targeting glioblastomas. VEGF antibody can be used for targeting esophageal cancer, breast cancer, and adenomatous polyposis. EGFR antibody can be used for targeting pancreatic cancer, brain neoplasms, gliomas, head and neck squamous cell carcinoma, and head and neck cancer. Carbonic anhydrase IX antibody can be used for targeting renal cell carcinomas.

In various examples, the fluorescence imaging agent may be provided as a lyophilized powder, solid, or liquid. In certain examples, the fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. In various examples, any diluent or carrier which will maintain the fluorescence imaging agent in solution may be used. As an example, ICG may be reconstituted with water. In some examples, once the fluorescence imaging agent is reconstituted, it may be mixed with additional diluents and carriers. In some examples, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although fluorescence imaging agents were described above in detail, other imaging agents may be used in connection with the systems, methods, and techniques described herein, depending on the medical imaging modality.

In some variations, the fluorescence imaging agent used in combination with the methods, systems and kits described herein may be used for blood flow imaging, tissue perfusion imaging, lymphatic imaging, or a combination thereof, which may be performed during an invasive surgical procedure, a minimally invasive surgical procedure, a non-invasive surgical procedure, or a combination thereof. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. In this regard, for example, a change in the wound over time, such as a change in wound dimensions (e.g., diameter, area), or a change in tissue perfusion in the wound and/or around the peri-wound, may be tracked over time with the application of the methods and systems. Examples of lymphatic imaging include identification of one or more lymph nodes, lymph node drainage, lymphatic mapping, or a combination thereof. In some variations, such lymphatic imaging may relate to the female reproductive system (e.g., uterus, cervix, vulva).

In variations relating to cardiac applications or any vascular applications, the imaging agent(s) (e.g., ICG alone or in combination with another imaging agent) may be injected intravenously. For example, the imaging agent may be injected intravenously through the central venous line, bypass pump and/or cardioplegia line and/or other vasculature to flow and/or perfuse the coronary vasculature, microvasculature and/or grafts. ICG may be administered as a dilute ICG/blood/saline solution down the grafted vessel or other vasculature such that the final concentration of ICG in the coronary artery or other vasculature depending on application is approximately the same or lower as would result from injection of about 2.5 mg (i.e., 1 ml of 2.5 mg/ml) into the central line or the bypass pump. The ICG may be prepared by dissolving, for example, 25 mg of the solid in 10 ml sterile aqueous solvent, which may be provided with the ICG by the manufacturer. One milliliter of the ICG solution may be mixed with 500 ml of sterile saline (e.g., by injecting 1 ml of ICG into a 500 ml bag of saline). Thirty milliliters of the dilute ICG/saline solution may be added to 10 ml of the subject's blood, which may be obtained in an aseptic manner from the central arterial line or the bypass pump. ICG in blood binds to plasma proteins and facilitates preventing leakage out of the blood vessels. Mixing of ICG with blood may be performed using standard sterile techniques within the sterile surgical field. Ten ml of the ICG/saline/blood mixture may be administered for each graft. Rather than administering ICG by injection through the wall of the graft using a needle, ICG may be administered by means of a syringe attached to the (open) proximal end of the graft. When the graft is harvested surgeons routinely attach an adaptor to the proximal end of the graft so that they can attach a saline filled syringe, seal off the distal end of the graft and inject saline down the graft, pressurizing the graft and thus assessing the integrity of the conduit (with respect to leaks, side branches etc.) prior to performing the first anastomosis. In other variations, the methods, dosages or a combination thereof as described herein in connection with cardiac imaging may be used in any vascular and/or tissue perfusion imaging applications.

Lymphatic mapping is an important part of effective surgical staging for cancers that spread through the lymphatic system (e.g., breast, gastric, gynecological cancers). Excision of multiple nodes from a particular node basin can lead to serious complications, including acute or chronic lymphedema, paresthesia, and/or seroma formation, when in fact, if the sentinel node is negative for metastasis, the surrounding nodes will most likely also be negative. Identification of the tumor draining lymph nodes (LN) has become an important step for staging cancers that spread through the lymphatic system in breast cancer surgery for example. LN mapping involves the use of dyes and/or radiotracers to identify the LNs either for biopsy or resection and subsequent pathological assessment for metastasis. The goal of lymphadenectomy at the time of surgical staging is to identify and remove the LNs that are at high risk for local spread of the cancer. Sentinel lymph node (SLN) mapping has emerged as an effective surgical strategy in the treatment of breast cancer. It is generally based on the concept that metastasis (spread of cancer to the axillary LNs), if present, should be located in the SLN, which is defined in the art as the first LN or group of nodes to which cancer cells are most likely to spread from a primary tumor. If the SLN is negative for metastasis, then the surrounding secondary and tertiary LN should also be negative. The primary benefit of SLN mapping is to reduce the number of subjects who receive traditional partial or complete lymphadenectomy and thus reduce the number of subjects who suffer from the associated morbidities such as lymphedema and lymphocysts.

The current standard of care for SLN mapping involves injection of a tracer that identifies the lymphatic drainage pathway from the primary tumor. The tracers used may be radioisotopes (e.g. Technetium-99 or Tc-99m) for intraoperative localization with a gamma probe. The radioactive tracer technique (known as scintigraphy) is limited to hospitals with access to radioisotopes require involvement of a nuclear physician and does not provide real-time visual guidance. A colored dye, isosulfan blue, has also been used, however this dye cannot be seen through skin and fatty tissue. In addition, blue staining results in tattooing of the breast lasting several months, skin necrosis can occur with subdermal injections, and allergic reactions with rare anaphylaxis have also been reported. Severe anaphylactic reactions have occurred after injection of isosulfan blue (approximately 2% of patients). Manifestations include respiratory distress, shock, angioedema, urticarial and pruritus. Reactions are more likely to occur in subjects with a history of bronchial asthma, or subjects with allergies or drug reactions to triphenylmethane dyes. Isosulfan blue is known to interfere with measurements of oxygen saturation by pulse oximetry and methemoglobin by gas analyzer. The use of isosulfan blue may result in transient or long-term (tattooing) blue coloration.

In contrast, fluorescence imaging in accordance with the various examples for use in SLN visualization, mapping, facilitates direct real-time visual identification of a LN and/or the afferent lymphatic channel intraoperatively, facilitates high-resolution optical guidance in real-time through skin and fatty tissue, visualization of blood flow, tissue perfusion or a combination thereof.

In some variations, visualization, classification or both of lymph nodes during fluorescence imaging may be based on imaging of one or more imaging agents, which may be further based on visualization and/or classification with a gamma probe (e.g., Technetium Tc-99m is a clear, colorless aqueous solution and is typically injected into the periareolar area as per standard care), another conventionally used colored imaging agent (isosulfan blue), and/or other assessment such as, for example, histology. The breast of a subject may be injected, for example, twice with about 1% isosulfan blue (for comparison purposes) and twice with an ICG solution having a concentration of about 2.5 mg/ml. The injection of isosulfan blue may precede the injection of ICG or vice versa. For example, using a TB syringe and a 30 G needle, the subject under anesthesia may be injected with 0.4 ml (0.2 ml at each site) of isosulfan blue in the periareolar area of the breast. For the right breast, the subject may be injected at 12 and 9 o'clock positions and for the left breast at 12 and 3 o'clock positions. The total dose of intradermal injection of isosulfan blue into each breast may be about 4.0 mg (0.4 ml of 1% solution: 10 mg/ml). In another exemplary variation, the subject may receive an ICG injection first followed by isosulfan blue (for comparison). One 25 mg vial of ICG may be reconstituted with 10 ml sterile water for injection to yield a 2.5 mg/ml solution immediately prior to ICG administration. Using a TB syringe and a 30 G needle, for example, the subject may be injected with about 0.1 ml of ICG (0.05 ml at each site) in the periareolar area of the breast (for the right breast, the injection may be performed at 12 and 9 o'clock positions and for the left breast at 12 and 3 o'clock positions). The total dose of intradermal injection of ICG into each breast may be about 0.25 mg (0.1 ml of 2.5 mg/ml solution) per breast. ICG may be injected, for example, at a rate of 5 to 10 seconds per injection. When ICG is injected intradermally, the protein binding properties of ICG cause it to be rapidly taken up by the lymph and moved through the conducting vessels to the LN. In some variations, the ICG may be provided in the form of a sterile lyophilized powder containing 25 mg ICG with no more than 5% sodium iodide. The ICG may be packaged with aqueous solvent consisting of sterile water for injection, which is used to reconstitute the ICG. In some variations the ICG dose (mg) in breast cancer sentinel lymphatic mapping may range from about 0.5 mg to about 10 mg depending on the route of administration. In some variations, the ICG does may be about 0.6 mg to about 0.75 mg, about 0.75 mg to about 5 mg, about 5 mg to about 10 mg. The route of administration may be for example subdermal, intradermal (e.g., into the periareolar region), subareolar, skin overlaying the tumor, intradermal in the areola closest to tumor, subdermal into areola, intradermal above the tumor, periareolar over the whole breast, or a combination thereof. The NIR fluorescent positive LNs (e.g., using ICG) may be represented as a black and white NIR fluorescence image(s) for example and/or as a full or partial color (white light) image, full or partial desaturated white light image, an enhanced colored image, an overlay (e.g., fluorescence with any other image), a composite image (e.g., fluorescence incorporated into another image) which may have various colors, various levels of desaturation or various ranges of a color to high-light/visualize certain features of interest. Processing of the images may be further performed for further visualization and/or other analysis (e.g., quantification). The lymph nodes and lymphatic vessels may be visualized (e.g., intraopera-tively, in real time) using fluorescence imaging systems and methods according to the various examples for ICG and SLNs alone or in combination with a gamma probe (Tc-99m) according to American Society of Breast Surgeons (ASBrS) practice guidelines for SLN biopsy in breast cancer patients. Fluorescence imaging for LNs may begin from the site of injection by tracing the lymphatic channels leading to the LNs in the axilla. Once the visual images of LNs are identified, LN mapping and identification of LNs may be done through incised skin, LN mapping may be performed until ICG visualized nodes are identified. For comparison, mapping with isosulfan blue may be performed until 'blue' nodes are identified. LNs identified with ICG alone or in combination with another imaging technique (e.g., isosulfan blue, and/or Tc-99m) may be labeled to be excised. Subject may have various stages of breast cancer (e.g., IA, IB, IIA).

In some variations, such as for example, in gynecological cancers (e.g., uterine, endometrial, vulvar and cervical malignancies), ICG may be administered interstitially for the visualization of lymph nodes, lymphatic channels, or a combination thereof. When injected interstitially, the protein binding properties of ICG cause it to be rapidly taken up by the lymph and moved through the conducting vessels to the SLN. ICG may be provided for injection in the form of a sterile lyophilized powder containing 25 mg ICG (e.g., 25 mg/vial) with no more than 5.0% sodium iodide. ICG may be then reconstituted with commercially available water (sterile) for injection prior to use. According to an example, a vial containing 25 mg ICG may be reconstituted in 20 ml of water for injection, resulting in a 1.25 mg/ml solution. A total of 4 ml of this 1.25 mg/ml solution is to be injected into a subject (4×1 ml injections) for a total dose of ICG of 5 mg per subject. The cervix may also be injected four (4) times with a 1 ml solution of 1% isosulfan blue 10 mg/ml (for comparison purposes) for a total dose of 40 mg. The injection may be performed while the subject is under anesthesia in the operating room. In some variations the ICG dose (mg) in gynecological cancer sentinel lymph node detection and/or mapping may range from about 0.1 mg to about 5 mg depending on the route of administration. In some variations, the ICG does may be about 0.1 mg to about 0.75 mg, about 0.75 mg to about 1.5 mg, about 1.5 mg to about 2.5 mg, about 2.5 mg to about 5 mg. The route of administration may be for example cervical injection, vulva peritumoral injection, hysteroscopic endometrial injection, or a combination thereof. In order to minimize the spillage of isosulfan blue or ICG interfering with the mapping procedure when LNs are to be excised, mapping may be performed on a hemi-pelvis, and mapping with both isosul-fan blue and ICG may be performed prior to the excision of any LNs. LN mapping for Clinical Stage I endometrial cancer may be performed according to the NCCN Guide-lines for Uterine Neoplasms, SLN Algorithm for Surgical Staging of Endometrial Cancer; and SLN mapping for Clinical Stage I cervical cancer may be performed according to the NCCN Guidelines for Cervical Neoplasms, Surgical/SLN Mapping Algorithm for Early-Stage Cervical Cancer. Identification of LNs may thus be based on ICG fluorescence imaging alone or in combination or co-administration with for a colorimetric dye (isosulfan blue) and/or radiotracer.

Visualization of lymph nodes may be qualitative and/or quantitative. Such visualization may comprise, for example, lymph node detection, detection rate, anatomic distribution of lymph nodes. Visualization of lymph nodes according to the various examples may be used alone or in combination with other variables (e.g., vital signs, height, weight, demo-graphics, surgical predictive factors, relevant medical his-tory and underlying conditions, histological visualization and/or assessment, Tc-99m visualization and/or assessment, concomitant medications). Follow-up visits may occur on the date of discharge, and subsequent dates (e.g., one month).

Lymph fluid comprises high levels of protein, thus ICG can bind to endogenous proteins when entering the lym-phatic system. Fluorescence imaging (e.g., ICG imaging) for lymphatic mapping when used in accordance with the meth-ods and systems described herein offers the following example advantages: high-signal to background ratio (or tumor to background ratio) as NIR does not generate sig-nificant autofluorescence, real-time visualization feature for lymphatic mapping, tissue definition (i.e., structural visual-ization), rapid excretion and elimination after entering the vascular system, and avoidance of non-ionizing radiation. Furthermore, NIR imaging has superior tissue penetration (approximately 5 to 10 millimeters of tissue) to that of visible light (1 to 3 mm of tissue). The use of ICG for example also facilitates visualization through the perito-neum overlying the para-aortic nodes. Although tissue fluo-rescence can be observed with NIR light for extended periods, it cannot be seen with visible light and consequently does not impact pathologic evaluation or processing of the LN. Also, florescence is easier to detect intra-operatively than blue staining (isosulfan blue) of lymph nodes. In other variations, the methods, dosages or a combination thereof as described herein in connection with lymphatic imaging may be used in any vascular and/or tissue perfusion imaging applications.

Tissue perfusion relates to the microcirculatory flow of blood per unit tissue volume in which oxygen and nutrients are provided to and waste is removed from the capillary bed of the tissue being perfused. Tissue perfusion is a phenom-enon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels. In some examples, quantification of a target tissue may include calculating or determining a parameter or an amount related to the target tissue, such as a rate, size volume, time, distance/time, and/or volume/time, and/or an amount of change as it relates to any one or more of the preceding parameters or amounts. However, compared to blood move-ment through the larger diameter blood vessels, blood move-ment through individual capillaries can be highly erratic, principally due to vasomotion, wherein spontaneous oscillation in blood vessel tone manifests as pulsation in erythrocyte movement.

One or more examples are directed to a fluorescence imaging agent for use in the imaging systems and methods as described herein. In one or more examples, the use may comprise blood flow imaging, tissue perfusion imaging, lymphatic imaging, or a combination thereof, which may occur during an invasive surgical procedure, a minimally invasive surgical procedure, a non-invasive surgical procedure, or a combination thereof. The fluorescence agent may be included in the kit described herein.

In one or more examples, the invasive surgical procedure may comprise a cardiac-related surgical procedure or a reconstructive surgical procedure. The cardiac-related surgical procedure may comprise a cardiac coronary artery bypass graft (CABG) procedure which may be on pump and/or off pump.

In one or more examples, the minimally invasive or the non-invasive surgical procedure may comprise a wound care procedure.

In one or more examples, the lymphatic imaging may comprise identification of a lymph node, lymph node drainage, lymphatic mapping, or a combination thereof. The lymphatic imaging may relate to the female reproductive system.

The methods and processes described herein may be performed by code or instructions to be executed by a computer, processor, manager, or controller, or in hardware or other circuitry. Because the algorithms that form the basis of the methods (or operations of the computer, processor, or controller) are described in detail, the code or instructions for implementing the operations of the method examples may transform the computer, processor, or controller into a special-purpose processor for performing the methods described herein.

Also, another example may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, or controller which is to execute the code or instructions for performing the method examples described herein.

The foregoing description, for the purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated. For the purpose of clarity and a concise description, features are described herein as part of the same or separate examples; however, it will be appreciated that the scope of the disclosure includes examples having combinations of all or some of the features described.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method of visualizing tissue of a subject, the method comprising: receiving a fluorescence image of the tissue of the subject comprising a plurality of intensity values, wherein a first portion of the plurality of intensity values is associated with a first fluorescence emission that is from fluorescence agent that is preferentially accumulated or activated in a target region in the tissue, and a second portion of the plurality of intensity values is associated with a second fluorescence emission that is from fluorescence agent that is not located within the target region in the tissue; analyzing the plurality of intensity values to determine a set of local maximum intensity values from the plurality of intensity values; generating an enhanced fluorescence image by applying a nonlinear contrast mapping to the plurality of intensity values, wherein the nonlinear contrast mapping is based on the set of local maximum intensity values; displaying the enhanced fluorescence image, wherein contrast in the enhanced fluorescence image is increased between the target region in the tissue and non-target regions in the tissue; and diagnosing and/or treating at least a portion of the target region in the tissue based on the displayed enhanced fluorescence image.

2. The method of claim 1, wherein the set of local maximum intensity values comprises intensity values of the plurality of intensity values that exceed a predefined threshold.

3. The method of claim 2, wherein the predefined threshold is at least 90% of a maximum intensity value in the fluorescence image.

4. The method of claim 1, wherein analyzing the plurality of intensity values to determine the set of local maximum intensity values comprises applying non-maximum suppression to the plurality of intensity values.

5. The method of claim 1, wherein applying the nonlinear contrast mapping to the plurality of intensity values comprises applying a distance transform to the plurality of intensity values.

6. The method of claim 5, wherein the distance transform is based on an average intensity value of the set of local maximum intensity values.

7. The method of claim 5, wherein the distance transform is based on an average intensity value of pixels of the plurality of pixels that have an intensity value greater than or equal to a predetermined intensity level.

8. The method of claim 1, wherein applying the nonlinear contrast mapping to the plurality of intensity values generates a plurality of mapped values, and generating the enhanced fluorescence image comprises applying a smoothing filter to the plurality of mapped values.

9. The method of claim 8, wherein the smoothing filter is a low pass Gaussian filter.

10. The method of claim 1, wherein the fluorescence image is received from an imaging system.

11. The method of claim 1, wherein the fluorescence image is received from a memory.

12. The method of claim 1, wherein the enhanced fluorescence image is displayed intraoperatively.

13. The method of claim 1, wherein displaying the enhanced fluorescence image comprises displaying the enhanced fluorescence image in combination with a visible light image.

14. The method of claim 13, wherein displaying the enhanced fluorescence image in combination with the visible light image comprises overlaying the enhanced fluorescence image on the visible light image.

15. The method of claim 1, wherein diagnosing or treating the at least a portion of the target region in the tissue based on the displayed enhanced fluorescence image comprises locating a tumor based on the displayed enhanced fluorescence image.

16. The method of claim 1, wherein diagnosing or treating the at least a portion of the target region in the tissue based on the displayed enhanced fluorescence image comprises removing the at least a portion of the target tissue based on the displayed enhanced fluorescence image.

17. A system for visualizing tissue of a subject, the system comprising:

a display;

one or more processors;

memory; and one or more programs, wherein the one or more programs are stored in the memory and configured to be executed by the one or more processors, the one or more programs including instructions for:

receiving a fluorescence image of the tissue of the subject comprising a plurality of intensity values, wherein a first portion of the plurality of intensity values is associated with a first fluorescence emission that is from fluorescence agent that is preferentially accumulated or activated in a target region in the tissue, and a second portion of the plurality of intensity values is associated with a second fluorescence emission that is from fluorescence agent that is not located within the target region in the tissue;

analyzing the plurality of intensity values to determine a set of local maximum intensity values from the plurality of intensity values;

generating an enhanced fluorescence image by applying a nonlinear contrast mapping to the plurality of intensity values, wherein the nonlinear contrast mapping is based on the set of local maximum intensity values; and displaying the enhanced fluorescence image, wherein contrast in the enhanced fluorescence image is increased between the target region in the tissue and non-target regions in the tissue, wherein the displayed enhanced fluorescence image is configured to be used to diagnose and/or treat at least a portion of the target region.

18. The system of claim 17, comprising a light source for providing fluorescence excitation light to the tissue of the subject.

19. The system of claim 17, comprising an imager for generating the fluorescence image.

20. A non-transitory computer readable storage medium storing one or more programs for execution by one or more processors of a system for visualizing tissue of a subject, the one or more programs comprising instructions for causing the system to:

receive a fluorescence image of the tissue of the subject comprising a plurality of intensity values, wherein a first portion of the plurality of intensity values is associated with a first fluorescence emission that is from fluorescence agent that is preferentially accumulated or activated in a target region in the tissue, and a second portion of the plurality of intensity values is associated with a second fluorescence emission that is from fluorescence agent that is not located within the target region in the tissue;

analyze the plurality of intensity values to determine a set of local maximum intensity values from the plurality of intensity values;

generate an enhanced fluorescence image by applying a nonlinear contrast mapping to the plurality of intensity values, wherein the nonlinear contrast mapping is based on the set of local maximum intensity values; and display the enhanced fluorescence image, wherein contrast in the enhanced fluorescence image is increased between the target region in the tissue and non-target regions in the tissue, wherein the displayed enhanced fluorescence image is configured to be used to diagnose and/or treat at least a portion of the target region.

* * * * *